(12) United States Patent
Li et al.

(10) Patent No.: US 8,486,712 B2
(45) Date of Patent: Jul. 16, 2013

(54) DEUTERIUM ISOBARIC TAG REAGENTS FOR QUANTITATIVE ANALYSIS

(75) Inventors: Shuwei Li, Rockville, MD (US); Dexing Zeng, St. Louis, MO (US)

(73) Assignee: University of Maryland, College Park, College Park, MD (US)

( * ) Notice: Subject to any disclaimer, the term of this patent is extended or adjusted under 35 U.S.C. 154(b) by 13 days.

(21) Appl. No.: 13/255,849

(22) PCT Filed: Mar. 10, 2010

(86) PCT No.: PCT/US2010/026868
§ 371 (c)(1),
(2), (4) Date: Sep. 9, 2011

(87) PCT Pub. No.: WO2010/104981
PCT Pub. Date: Sep. 16, 2010

(65) Prior Publication Data
US 2011/0318771 A1 Dec. 29, 2011

Related U.S. Application Data

(60) Provisional application No. 61/158,932, filed on Mar. 10, 2009.

(51) Int. Cl.
*G01N 33/68* (2006.01)
*C07D 207/46* (2006.01)

(52) U.S. Cl.
USPC .......................................... 436/173; 548/542

(58) Field of Classification Search
USPC ........................................ 436/173; 548/542
See application file for complete search history.

(56) References Cited

U.S. PATENT DOCUMENTS

| | | | |
|---|---|---|---|
| 5,254,730 A | 10/1993 | Kilgore | |
| 5,272,054 A | 12/1993 | Switchenko et al. | |
| 6,287,780 B1 | 9/2001 | Schmidt et al. | |
| 6,629,040 B1 | 9/2003 | Goodlett et al. | |
| 6,699,668 B1 | 3/2004 | Schmidt et al. | |
| 7,195,751 B2 | 3/2007 | Pappin et al. | |
| 7,294,456 B2 | 11/2007 | Schmidt et al. | |
| 7,799,576 B2 | 9/2010 | Pappin et al. | |
| 7,816,304 B2 | 10/2010 | Schmidt et al. | |
| 7,825,069 B2 | 11/2010 | Schmidt et al. | |
| 7,868,547 B2 | 1/2011 | Pappin et al. | |
| 7,910,059 B2 | 3/2011 | Pappin et al. | |
| 7,947,513 B2 | 5/2011 | Pappin et al. | |
| 7,982,070 B2 | 7/2011 | Smith et al. | |
| 2005/0042625 A1 | 2/2005 | Schmidt et al. | |
| 2005/0148087 A1 | 7/2005 | Pappin et al. | |
| 2006/0105416 A1 | 5/2006 | Pappin et al. | |
| 2006/0172319 A1 | 8/2006 | Yan et al. | |
| 2006/0183238 A1 | 8/2006 | Nimkar et al. | |
| 2007/0037286 A1 | 2/2007 | Purkayastha | |
| 2007/0048752 A1 | 3/2007 | Yan et al. | |
| 2010/0093011 A1 | 4/2010 | Nimkar et al. | |
| 2010/0136703 A1 | 6/2010 | Purkayastha | |
| 2010/0178710 A1 | 7/2010 | Hamon et al. | |
| 2010/0311175 A1 | 12/2010 | Yan et al. | |
| 2011/0045516 A1 | 2/2011 | Pappin et al. | |
| 2011/0217720 A1 | 9/2011 | Pappin et al. | |

FOREIGN PATENT DOCUMENTS

| | | |
|---|---|---|
| EP | 1400599 A1 | 3/2004 |
| EP | 1806586 A1 | 7/2007 |
| WO | 9831830 A1 | 7/1998 |
| WO | 9932501 A1 | 7/1999 |
| WO | 0168664 A2 | 9/2001 |
| WO | 2005037853 A2 | 4/2005 |
| WO | 2006086540 A1 | 8/2006 |
| WO | 2007012849 A2 | 2/2007 |
| WO | 2007100506 A2 | 7/2007 |

*Primary Examiner* — Robert Havlin
(74) *Attorney, Agent, or Firm* — Hultquist, PLLC; Steven J. Hultquist; Kelly K. Reynolds

(57) ABSTRACT

Deuterium isobaric tag reagents are provided for the quantitation of biomolecules, where the reagents contain heavy isotope atoms, including one or more $^2H$ in each reagent. Generally, the reagents are described by the formula: reporter group—balancer group—reactive group, wherein the reporter group and the balancer group are linked by an MS/MS scissionable bond. Each of the reporter group and balancer groups independently contain 0 to 9 heavy isotope atoms selected from $^{13}C$, $^{15}N$ and $^2H$ and the total number of $^2H$ atoms in each reagent is 1 to 6. The mass of the reporter group is from 114-123 Daltons. Exemplary deuterium isobaric tag reagents include Di-ART, DiART-t-I, DiART-t-Br and DiART-t-M. Also provided are compositions containing more than one deuterium isobaric tag reagent and methods for making and using deuterium isobaric tag reagents.

19 Claims, 10 Drawing Sheets

DiART

DiART-t-Br

DiART-t-I

DiART-t-M

| Tag | Position 1 | Position 2 | Position 3 | Position 4 | Position 6 | Position7 |
|---|---|---|---|---|---|---|
| DiART[5]-114 | CH$_3$ | CH$_3$ | $^{14}$N | $^{13}$C | CD$_2$ | CD$_2$ |
| DiART[5]-115 | CH$_3$ | CH$_3$ | $^{15}$N | $^{12}$C | CD$_2$ | CD$_2$ |
| DiART[5]-116 | CH$_2$D | CH$_2$D | $^{14}$N | $^{13}$C | CD$_2$ | CH$_2$ |
| DiART[5]-117 | CH$_2$D | CH$_2$D | $^{15}$N | $^{12}$C | CD$_2$ | CH$_2$ |
| DiART[5]-118 | CHD$_2$ | CHD$_2$ | $^{14}$N | $^{13}$C | CH$_2$ | CH$_2$ |
| DiART[5]-119 | CHD$_2$ | CHD$_2$ | $^{15}$N | $^{12}$C | CH$_2$ | CH$_2$ |

FIG. 7

Mascot Search Results

```
User          : Mascot Daemon
Email         : daemon@localhost
Search title  : Submitted from DiART6plex-3protein by Mascot Daemon on LIN-XP
MS data file  : E:\Laboratory\Projects\Proteomics\DiART\MultiFile2.mgf
Database      : NCBInr 20070216 (4626864 sequences; 1596579197 residues)
Quantitation  : DiART6plex method details
              : Omic Biosystems DiART 6-plex reagent
Timestamp     : 18 Feb 2009 at 17:51:58 GMT
Protein hits  : 115/114  116/114  117/114  118/114  119/114
```

| | | | | | | |
|---|---|---|---|---|---|---|
| 0.996 | 1.022 | 1.056 | 1.025 | 0.996 | gi|63052 | unnamed protein product [Gallus gallus] |
| 1.017 | 1.053 | 1.056 | 1.042 | 1.044 | gi|229752 | catalase |
| | | | | | gi|1351867 | Serum albumin precursor (Allergen Bos d 6) (BSA) |

Probability Based Mowse Score

Ions score is -10*Log(P), where P is the probability that the observed match is a random event.
Individual ions scores > 51 indicate identity or extensive homology (p<0.05).
Protein scores are derived from ions scores as a non-probabilistic basis for ranking protein hits.

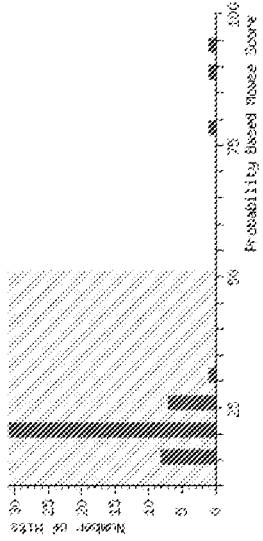

Peptide Summary Report

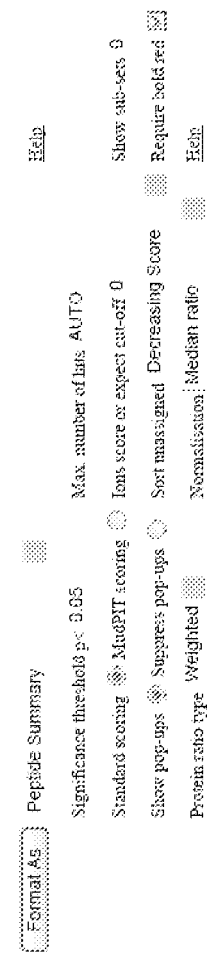

```
Type of search        : MS/MS Ion Search
Enzyme                : Trypsin
Fixed modifications   : Carbamidomethyl (C),DiART6plex (K),DiART6plex (N-term),DiART6plex (K),DiART6plex (N-term)
Mass values           : Monoisotopic
Protein Mass          : Unrestricted
Peptide Mass Tolerance: ± 0.8 Da
Fragment Mass Tolerance: ± 0.8 Da
Max Missed Cleavages  : 1
Instrument type       : MALDI-TOF-TOF
Number of Queries     : 6
```

US 8,486,712 B2

DEUTERIUM ISOBARIC TAG REAGENTS FOR QUANTITATIVE ANALYSIS

CROSS REFERENCE TO RELATED APPLICATIONS

This application is a U.S. national phase application under the provisions of 35 U.S.C. §371 of International Patent Application No. PCT/US10/26868 filed Mar. 10, 2010, which in turn claims the benefit of priority of U.S. Provisional Patent Application No. 61/158,932, filed Mar. 10, 2009 in the names of Shuwei Li and Dexing Zeng for "DiART (DEUTERIUM ISOBARIC AMINE REACTIVE TAG) REAGENTS FOR QUANTITATIVE PROTEOMICS." The disclosures of International Patent Application No. PCT/US10/26868 and U.S. Provisional Patent Application 61/158,932 are hereby incorporated herein by reference in their respective entireties for all purposes.

FIELD OF THE INVENTION

The present invention relates to reagents for the analysis of biological matter, more particularly reagents for the analysis of biomolecules by quantitation. The deuterium isobaric tag reagents comprise heavy isotope atoms, including one or more $^2$H in each reagent. The invention also relates to compositions of more than one deuterium isobaric tag reagent. Also provided are methods for making and using deuterium isobaric tag reagents.

BACKGROUND OF THE INVENTION

Mass Spectrometry (MS)-based quantitative proteomics is a robust technology for the systematic understanding of biological processes. Several MS-based methods, using either stable isotope-labeling or label-free strategies, have been developed to improve the throughput and accuracy of protein quantitation. The stable-isotope labeling methods rely on the introduction of stable isotope tags to proteins, and the labeled proteins can be distinguished and quantified by MS. Label-free quantitation is performed by spectral count and statistical analysis of unlabeled proteolytic peptides. Although label-free methods are implemented without incurring additional reagent costs, isotope label-based strategies can provide more accurate quantitation and capabilities of processing multiple specimens in parallel. This has been demonstrated by commercially available 8-plex iTRAQ (Isobaric Tag for Relative and Absolute Quantitation) and 6-plex TMT (Tandem Mass Tag) reagents.

Stable isotope labeling methods, such as ICAT (Isotope Coded Affinity Tag), iTRAQ (Isobaric Tag for Relative and Absolute Quantitation), and SILAC (Stable Isotope Labeling with Amino Acids in Cell Culture), are widely used for the quantitative comparison of proteins, providing versatile tools for proteomics research and biomarker discovery. (Ong, S. E.; Mann, M. Nat Chem. Biol. 2005, 1, 252-62; Yan, W.; Chen, S. S. Brief Funct. Genomic Proteomic 2005, 4, 27-38; Julka, S.; Regnier, F. E. Brief Funct. Genomic Proteomic 2005, 4, 158-77.)

Known isotope labeling methods use reagents that are coded with common isotope pairs, including $^2$H/$^1$H, $^{13}$C/$^{12}$C, and $^{15}$N/$^{14}$N, to label identical peptides or proteins to make them distinguishable by MS. (Ong, S. E.; Blagoev, B.; Kratchmarova, I.; Kristensen, D. B.; Steen, H.; Pandey, A.; Mann, M. Mol Cell Proteomics 2002, 1, 376-86; Ross, P. L. et al. Mol Cell Proteomics 2004, 3, 1154-69; Li, S.; Zeng, D. Chem. Commun. 2007, 2181-3; Wiese, S.; Reidegeld, K. A.; Meyer, H. E.; Warscheid, B. Proteomics 2007, 7, 340-50.)

Unfortunately, known reagents are prohibitively expensive (for example, iTRAQ 8-plex 1-assay kit from Applied Biosystems, $595.00 USD; TMT 6-plex 5-assay kit from Thermo Fisher Scientific Inc, $2300.00 USD), limiting their use in basic biological studies and clinical applications where a large number of samples need to be processed. The high costs of these reagents are due, in part, to the fact that they are coded with expensive $^{13}$C, $^{15}$N or $^{18}$O, but not with the less expensive $^2$H. Additionally, the preparation of iTRAQ and TMT reagents is quite complicated and requires expensive starting materials. For example, the synthesis of TMT reagents involves a daunting number of 14 steps with an overall yield less than 1%.

Though $^2$H-labeled molecules were developed as the prototype reagents in the first generation isotope labeling technologies (Gygi, S. P.; Rist, B.; Gerber, S. A.; Turecek, F.; Gelb, M. H.; Aebersold, R. Nat Biotechnol 1999, 17, 994-9), they have been largely phased out and replaced by $^{13}$C— or $^{15}$N-coded reagents because these early generation $^2$H coded reagents cause chromatographic shift in reverse phase HPLC and compromise the accuracy of quantitation by LC-MS/MS. (Yi, E. C.; Li, X. J.; Cooke, K.; Lee, H.; Raught, B.; Page, A.; Aneliunas, V.; Hieter, P.; Goodlett, D. R.; Aebersold, R. Proteomics 2005, 5, 380-7.)

However, as $^2$H-labeled compounds are usually easier and less expensive to synthesize than their $^{13}$C— or $^{15}$N-coded counterparts, it is still of great interest to develop $^2$H-based technologies for protein quantitation, if $^2$H-related chromatographic shift could be eliminated. Recently, a study to identify structural features of $^2$H-containing molecules that are responsible for their isotope effects has found that placing $^2$H atoms next to hydrophilic groups and minimizing the number of $^2$H atoms in a molecule can reduce their contribution to isotope effects, providing useful clues for the design of $^2$H-based tags that are irresolvable by HPLC. (Zhang, R.; Sioma, C. S.; Thompson, R. A.; Xiong, L.; Regnier, F. E. Anal Chem 2002, 74, 3662-9.)

There therefore remains a need in the art to develop $^2$H-based reagents and products containing such reagents for biomolecular quantitation. Cost effective and low complexity methods of making such reagents are also needed.

SUMMARY OF THE INVENTION

The present invention relates to deuterium isobaric tag reagents useful in the analysis of biomolecules and methods of making and using the deuterium isobaric tag reagents.

In one aspect, the invention relates to a deuterium isobaric tag reagent comprising the formula: reporter group–balancer group–reactive group, where the reporter group and the balancer group are linked by an MS/MS scissionable bond, easily fragmented in MS/MS, the reporter group comprises 0 to 9 heavy isotope atoms selected from $^{13}$C, $^{15}$N and $^2$H, the balancer group comprises 0 to 9 heavy isotope atoms selected from $^{13}$C, $^{15}$N and $^2$H, the reagent contains 1 to 6 $^2$H atoms, the mass of the reporter group is from 114-123 Daltons, and the reactive group is reactive with a biomolecule.

In another aspect the invention relates to a DiART reagent comprising the formula: reporter group–balancer group–reactive group, where the reporter group comprises $(CH_3)_2$—CH—$CH_2$—CH—$(N(CH_3)_2)$, the balancer group comprises CO—(NH)—$CH_2$—$CH_2$—CO, the reactive group comprises cyclo-N(CO—$CH_2$—$CH_2$—CO)—O, and the reagent has the structure:

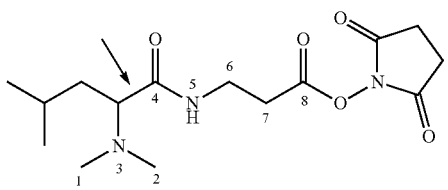 [SMILES: CC(C)CC(C(=O)NCCC(=O)ON1C(=O)CCC1=O)N(C)C]

wherein the reporter group and the balancer group are linked by a an MS/MS scissionable bond, easily fragmented in MS/MS, the reporter group comprises 0 to 9 heavy isotope atoms selected from $^{13}C$, $^{15}N$ and $^{2}H$, the balancer group comprises 0 to 9 heavy isotope atoms selected from $^{13}C$, $^{15}N$ and $^{2}H$, the reagent contains 1 to 6 $^{2}H$ atoms, and wherein the $CH_3$ at position 1 comprises 0 to 3 $^{2}H$ atoms and the C is selected from $^{12}C$ and $^{13}C$, the $CH_3$ at position 2 comprises 0 to 3 $^{2}H$ atoms and the C is selected from $^{12}C$ and $^{13}C$, the N at position 3 is selected from $^{14}N$ and $^{15}N$, the C at position 4 is selected from $^{12}C$ and $^{13}C$, the N at position 5 is selected from $^{14}N$ and $^{15}N$, the $CH_2$ at position 6 comprises 0 to 2 $^{2}H$ atoms and the C is selected from $^{12}C$ and $^{13}C$, the $CH_2$ at position 7 comprises 0 to 2 $^{2}H$ atoms and the C is selected from $^{12}C$ and $^{13}C$, the C at position 8 is selected from $^{12}C$ and $^{13}C$, and wherein the mass of the reporter group is 114-123 Daltons, the mass of the balancer group is 99-108 Daltons, and the sum of the mass of the reporter group and the balancer group is 214-222 Daltons.

In still another aspect the invention relates to DiART-like reagent comprising the formula: reporter group–balancer group–reactive group, where the reporter group comprises $(CH_3)_2CH-CH_2-CH(N(CH_3)_2)$, the balancer group comprises $CO-NH-CH_2-CH_2-NH$, the reactive group comprises $Br-CH_2-CO$ (DiART-t-Br), $I-CH_2-CO$ (DiART-t-I) or cyclo-$N(CO-CH=CH-CO)-CH_2-CH_2-CO$ (DiART-t-M), and the reagent is selected from structures a), b) and c):

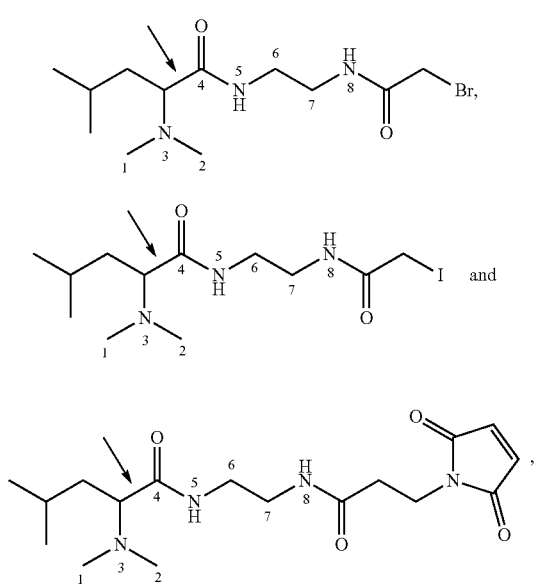

wherein the reporter group and the balancer group are linked by an MS/MS scissionable bond, easily fragmented in MS/MS, the reporter group comprises 0 to 9 heavy isotope atoms selected from $^{13}C$, $^{15}N$ and $^{2}H$, the balancer group comprises 0 to 9 heavy isotope atoms selected from $^{13}C$, $^{15}N$ and $^{2}H$, the reagent contains 1 to 6 $^{2}H$ atoms, and wherein the $CH_3$ at position 1 comprises 0 to 3 $^{2}H$ atoms and the C is selected from $^{12}C$ and $^{13}C$, the $CH_3$ at position 2 comprises 0 to 3 $^{2}H$ atoms and the C is selected from $^{12}C$ and $^{13}C$, the N at position 3 is selected from $^{14}N$ and $^{15}N$, the C at position 4 is selected from $^{12}C$ and $^{13}C$, the N at position 5 is selected from $^{14}N$ and $^{15}N$, the $CH_2$ at position 6 comprises 0 to 2 $^{2}H$ atoms and the C is selected from $^{12}C$ and $^{13}C$, the $CH_2$ at position 7 comprises 0 to 2 $^{2}H$ atoms and the C is selected from $^{12}C$ and $^{13}C$, the N at position 8 is selected from $^{14}N$ and $^{15}N$, and wherein the mass of the reporter group is 114-123 Daltons, the mass of the balancer group is 86-95, and the sum of the mass of the reporter group and the balancer group is 200-209 Daltons.

In a further aspect, the invention relates to compositions comprising two or more deuterium isobaric tag reagents of the invention.

A further aspect of the invention relates to use of deuterium isobaric tag reagents, alone or in combination with additional deuterium isobaric tag reagents in a method of biomolecular quantitation.

A still further aspect of the invention relates to a method of making a deuterium isobaric tag reagent of the invention.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
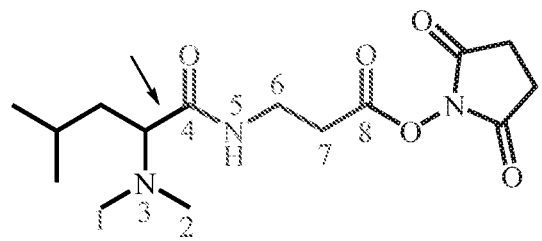
FIG. 1 provides the general structure of exemplary reagents of the invention, DiART, DiART-t-Br, DiART-t-M and DiART-t-I, where each contain a reporter group, a balancer group, and a reactive group and a bond that is easily fragmented in MS/MS between the reporter group and the balancer group, as indicated by an arrow.
Figure 1:
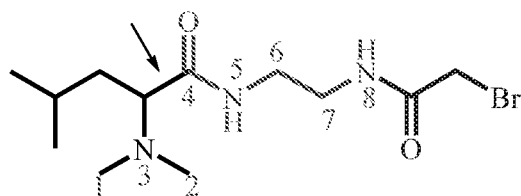
Figure 1:
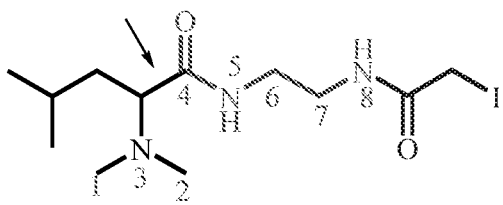
Figure 1:
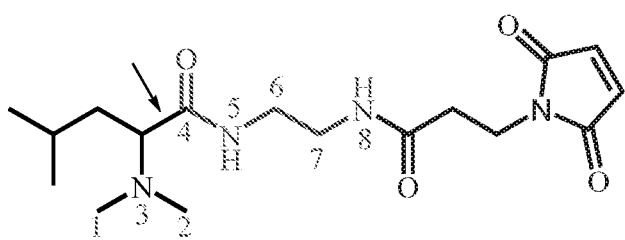

The present invention relates to deuterium isobaric tag reagents, which are $^{2}H$-based reagents and are useful in biomolecular quantitation. Specifically, the reagents of the invention are useful for labeling or tagging samples for analysis by quantitation methods.

"Quantitation" or "quantitative analysis" as used herein, refers to analysis of the composition of a sample. Quantitation allows identification of measurable properties of a sample subject to such analysis, such as the relative amounts of the elements of the sample, regardless of the source of the elements within the sample. Quantitation methods may include, but are not limited to high pressure liquid chromatography (HPLC), UV detection and mass spectrometry (MS).

The deuterium isobaric tag reagents of the invention contain one or more $^2$H atoms. In general, the deuterium isobaric tag reagents have the following formula:

reporter group–balancer group–reactive group wherein the reporter group and the balancer group are linked by an MS/MS scissionable bond, easily fragmented in MS/MS and wherein the reactive group reacts with a biomolecule.

The present inventors have discovered that the chromatographic isotope shift caused by early generation $^2$H labeled reagents relates mainly to the number of $^2$H atoms in each reagent. In general, the greater the difference in the number of $^2$H between two reagents, the larger the resulting chromatographic isotope shift observed. In contrast, each reagent of the invention can be formulated in different isotopic forms, where each isotopic form contains an identical number of $^2$H atoms. This design eliminates the chromatographic isotope shift and can be used to label biomolecular samples. In one embodiment, the deuterium isobaric tag reagents of the invention each contain 1 to 6 $^2$H atoms. In a particular embodiment the deuterium isobaric tag reagents of the invention each contain 4 $^2$H atoms.

In one embodiment of the invention the reporter group comprises 0 to 9 heavy isotope atoms selected from $^{13}$C, $^{15}$N and $^2$H and the balancer group comprises 0 to 9 heavy isotope atoms selected from $^{13}$C, $^{15}$N and $^2$H, and where the total number of $^2$H atoms in the reporter group and in the balancer group is 1 to 6 $^2$H atoms per molecule. In a specific embodiment, the total number of heavy isotope atoms in the reagent is five, four of which are $^2$H atoms.

A deuterium isobaric tag reagent of the invention with 1 heavy isotope may have a reporter group:balancer group ratio of heavy isotopes of 0:1 (where the reporter group has zero heavy isotope atoms and the balancer group has one heavy isotope atom) or 1:0 (where the reporter group has one heavy isotope atom and the balancer group has zero heavy isotope atoms). A deuterium isobaric tag reagent of the invention with 2 heavy isotopes may have a reporter group:balancer group ratio of heavy isotopes of 0:2, 1:1, or 2:0. A deuterium isobaric tag reagent of the invention with 3 heavy isotopes may have a reporter group:balancer group ratio of heavy isotopes of 0:3, 1:2, 2:1, or 3:0. A deuterium isobaric tag reagent of the invention with 4 heavy isotopes may have a reporter group:balancer group ratio of heavy isotopes of 0:4, 1:3, 2:2, 3:1, or 4:0. A deuterium isobaric tag reagent of the invention with 5 heavy isotopes may have a reporter group:balancer group ratio of heavy isotopes of 0:5, 1:4, 2:3, 3:2, 4:1, or 5:0. A deuterium isobaric tag reagent of the invention with 6 heavy isotopes may have a reporter group:balancer group ratio of heavy isotopes of 0:6, 1:5, 2:4, 3:3, 4:2, 5:1, or 6:0. A deuterium isobaric tag reagent of the invention with 7 heavy isotopes may have a reporter group:balancer group ratio of heavy isotopes of 0:7, 1:6, 2:5, 3:4, 4:3, 5:2, 6:1, or 7:0. A deuterium isobaric tag reagent of the invention with 8 heavy isotopes may have a reporter group:balancer group ratio of heavy isotopes of 0:8, 1:7, 2:6, 3:5, 4:4, 5:3, 6:2, 7:1, or 8:0. A deuterium isobaric tag reagent of the invention with 9 heavy isotopes may have a reporter group:balancer group ratio of heavy isotopes of 0:9, 1:8, 2:7, 3:6, 4:5, 5:4, 6:3, 7:2, 8:1, or 9:0.

Where deuterium isobaric tag reagents of the invention are isotopic forms of one another, the selection of substituents in each of the reporter group and balancer group is made such that the change in mass attributable to the selection of substituents in the reporter group is offset by the change in mass attributable to the selection of substituents in the balancer group. Accordingly, varying isotopic forms of a reagent will have the same total sum of the mass of the reporter group plus the mass of the balancer group. The reactive group of a deuterium isobaric tag reagent of the invention is selected to react with a biomolecule of interest. In one embodiment the reactive group of deuterium isobaric tag reagent of the invention is reactive with a functional group on the biomolecule. In another embodiment the functional group is selected from an amine group, a thiol group, a hydroxyl group, and an imine group. In still another embodiment the biomolecule is selected from a protein, a peptide, a small molecule metabolite, a lipid, a nucleic acid, a cell sample, a tissue sample and a biological fluid sample.

The deuterium isobaric tag reagents of the invention are useful in labeling or tagging samples for analysis by quantitation methods. In one embodiment of the invention, a group of reagents is used in a quantitation method, where each reagent in the group of reagents is a structurally identical molecule, each containing a reporter, a balancer, and a reactive group, where the molecules vary only by isotope composition. The total mass of any of the reagents in the group of reagents is equal to the total mass of any of the other isotopic variants.

Figure 2:
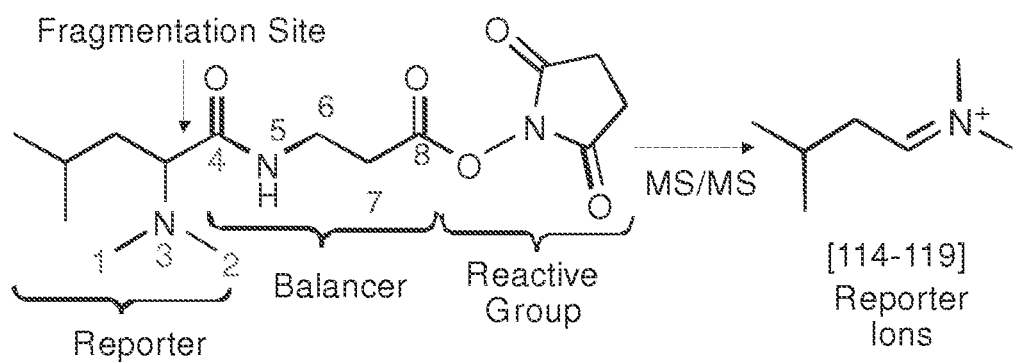
FIG. 2 provides the general structure of a DiART reagent, demonstrating each of the reporter group, balancer group, and reactive group. The table illustrates those positions containing heavy isotope atoms ($^{15}N$, $^{13}C$, $^{2}H=D$) in each reagent, shown in bold. When these reagents are fragmented in MS/MS, they generate strong reporter ions ranging from 114 to 119 Daltons.

An exemplary reagent of the invention is a deuterium isobaric amine reactive tag (DiART) reagent of the following formula:

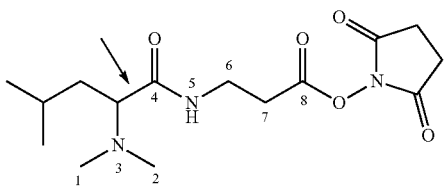 [SMILES: CC(C)CC(C(=O)NCCC(=O)ON1C(=O)CCC1=O)N(C)C]

where any of positions 1-8 may comprise heavy isotope atoms and where the arrow indicates the fragmentation site between the reporter group and the balancer group (FIG. 2).

In the DiART reagents, the reporter group is $(CH_3)_2$—CH—$CH_2$—CH—$(N(CH_3)_2)$, the balancer group is CO—(NH)—$CH_2$—$CH_2$—CO, and the reactive group is cyclo-N(CO—$CH_2$—$CH_2$—CO)—O. The reporter group and the balancer group are linked by an MS/MS scissionable bond, the reporter group comprises 0 to 9 heavy isotope atoms selected from $^{13}$C, $^{15}$N and $^2$H, the balancer group comprises 0 to 9 heavy isotope atoms selected from $^{13}$C, $^{15}$N and $^2$H, and the reagent contains one or more $^2$H atoms. The $CH_3$ at position 1 has 0 to 4 heavy isotope atoms, selected from $^{13}$C and $^2$H; the $CH_3$ at position 2 has 0 to 4 heavy isotope atoms, selected from $^{13}$C and $^2$H; the N at position 3 is selected from $^{14}$N and $^{15}$N; the C at position 4 is selected from $^{12}$C and $^{13}$C; the N at position 5 is selected from $^{14}$N and $^{15}$N; the $CH_2$ at position 6 has 0 to 3 heavy isotope atoms, selected from $^{13}$C and $^2$H; the $CH_2$ at position 7 has 0 to 3 heavy isotope atoms, selected from $^{13}C$ and $^2H$ and the C at position 8 is selected from $^{12}C$ and $^{13}C$. The mass of the reporter group is 114-123 Daltons, the mass of the balancer group is 99-108 Daltons, and the sum of the mass of the reporter group and the balancer group is 213-222 Daltons. A DiART reagent of the invention with 1 heavy isotope has a reporter group with a mass of 114-115 Daltons and a balancer group with a mass of 99-100 Daltons, and the total mass of the reporter group and the balancer group is 214 Daltons. A DiART reagent of the invention with 2 heavy isotopes has a reporter group with a mass of 114-116 Daltons and a balancer group with a mass of 99-101 Daltons, and the total mass of the reporter group and the balancer group is 215 Daltons. A DiART reagent of the invention with 3 heavy isotopes has a reporter group with a mass of 114-117 Daltons and a balancer group with a mass of 99-102 Daltons, and the total mass of the reporter group and the balancer group is 216 Daltons. A DiART reagent of the invention with 4 heavy isotopes has a reporter group with a mass of 114-118 Daltons and a balancer group with a mass of 99-103 Daltons, and the total mass of the reporter group and the balancer group is 217 Daltons. A DiART reagent of the invention with 5 heavy isotopes has a reporter group with a mass of 114-119 Daltons and a balancer group with a mass of 99-104 Daltons, and the total mass of the reporter group and the balancer group is 218 Daltons. A DiART reagent of the invention with 6 heavy isotopes has a reporter group with a mass of 114-120 Daltons and a balancer group with a mass of 99-105 Daltons, and the total mass of the reporter group and the balancer group is 219 Daltons. A DiART reagent of the invention with 7 heavy isotopes has a reporter group with a mass of 114-121 Daltons and a balancer group with a mass of 99-106 Daltons, and the total mass of the reporter group and the balancer group is 220 Daltons. A DiART reagent of the invention with 8 heavy isotopes has a reporter group with a mass of 114-122 Daltons and a balancer group with a mass of 99-107 Daltons, and the total mass of the reporter group and the balancer group is 221 Daltons. A DiART reagent of the invention with 9 heavy isotopes has a reporter group with a mass of 114-123 Daltons and a balancer group with a mass of 99-108 Daltons, and the total mass of the reporter group and the balancer group is 222 Daltons.

In another embodiment the invention provides a group of DiART reagents, which are structurally identical and vary only by isotope composition. The selection of substituents in each of the reporter group and balancer group is made such that the change in mass attributable to the selection of substituents in the reporter group is offset by the change in mass attributable to the selection of substituents in the balancer group, and where the sum of the mass of the reporter group and the balancer group is equal in each of the isotopic variants.

In an exemplary embodiment, a DiART reagent has five heavy isotope atoms, four of which are $^2H$ atoms. Substituents in the reporter group of a DiART reagent are selected such that the mass of the reporter group is in the range of 114-119 Daltons, while the substituents of the balancer group of a DiART reagent are selected such that the mass of the balancer group is 99-104 Daltons and the sum of the mass of the reporter group and the balancer group is 218 Daltons.

In the exemplary embodiment, a group of six reagents can be prepared, where each of the DiART reagents is structurally identical, each containing a reporter, a balancer, and a reactive group, where the molecules vary only by isotope composition. Each reagent contains five heavy isotope atoms. In DiART-114, the mass of the reporter group is 114 Daltons and the mass of the balancer group is 104 Daltons. In DiART-115, the mass of the reporter group is 115 Daltons and the mass of the balancer group is 103 Daltons. In DiART-116, the mass of the reporter group is 116 Daltons and the mass of the balancer group is 102 Daltons. In DiART-117, the mass of the reporter group is 117 Daltons and the mass of the balancer group is 101 Daltons. In DiART-118, the mass of the reporter group is 118 Daltons and the mass of the balancer group is 100 Daltons. In DiART-119, the mass of the reporter group is 119 Daltons and the mass of the balancer group is 99 Daltons. When the resulting reagents are fragmented in MS/MS, they generate strong reporter ions with MS peaks ranging from 114 to 119. Each of the reagents, termed $DiART^5$-114 to $DiART^5$-119, is set forth in Table 1 below:

TABLE 1

| Reagent | Position 1 | Position 2 | Position 3 | Position 4 | Position 6 | Position 7 |
|---|---|---|---|---|---|---|
| $DiART^5$-114 | $CH_3$ | $CH_3$ | $^{14}N$ | $^{13}C$ | $CD_2$ | $CD_2$ |
| $DiART^5$-115 | $CH_3$ | $CH_3$ | $^{15}N$ | $^{12}C$ | $CD_2$ | $CD_2$ |
| $DiART^5$-116 | $CH_2$D | $CH_2$D | $^{14}N$ | $^{13}C$ | $CD_2$ | $CH_2$ |
| $DiART^5$-117 | $CH_2$D | $CH_2$D | $^{15}N$ | $^{12}C$ | $CD_2$ | $CH_2$ |
| $DiART^5$-118 | $CH$$D_2$ | $CH$$D_2$ | $^{14}N$ | $^{13}C$ | $CH_2$ | $CH_2$ |
| $DiART^5$-119 | $CH$$D_2$ | $CH$$D_2$ | $^{15}N$ | $^{12}C$ | $CH_2$ | $CH_2$ |

Those positions containing heavy isotope atoms ($^{15}N$, $^{13}C$, $^2H$ = D) in each reagent are shown in bold.

The total mass of any of the DiART reagents with five heavy isotope atoms, four of which are $^2H$ atoms reagents, is 332 Daltons (332.2079 Daltons when containing a $^{13}C$ or 332.2016 when containing a $^{15}N$). While a group of six DiART reagents is provided as an exemplary embodiment herein, the invention also contemplates groups of additional numbers of DiART reagents that are isotopic variants of one another, where the sum of the mass of the reporter group and the balancer group is equal in each of the isotopic variants.

In another exemplary embodiment a group of ten reagents can be prepared, where each of the DiART reagents is structurally identical, each containing a reporter, a balancer, and a reactive group, where the molecules vary only by isotope composition. Each reagent contains five heavy isotope atoms. Exemplary reagents, termed $DiART^9$-114 to $DiART^9$-123, is set forth in Table 2 below:

TABLE 2

| Reagent | Position 1 | Position 2 | Position 3 | Position 4 | Position 5 | Position 6 | Position 7 | Position 8 |
|---|---|---|---|---|---|---|---|---|
| $DiART^9$-114 | $CH_3$ | $CH_3$ | N | $^{13}C$ | $^{15}N$ | $^{13}CD_2$ | $^{13}CD_2$ | $^{13}C$ |
| $DiART^9$-115 | $CH_3$ | $CH_3$ | $^{15}N$ | C | $^{15}N$ | $^{13}CD_2$ | $^{13}CD_2$ | $^{13}C$ |
| $DiART^9$-116 | $C$D$H_2$ | $C$D$H_2$ | N | $^{13}C$ | $^{15}N$ | $^{13}CH_2$ | $^{13}CD_2$ | $^{13}C$ |

TABLE 2-continued

| Reagent | Position 1 | Position 2 | Position 3 | Position 4 | Position 5 | Position 6 | Position 7 | Position 8 |
|---|---|---|---|---|---|---|---|---|
| DiART$^9$-117 | CDH$_2$ | CDH$_2$ | $^{15}$N | C | $^{15}$N | $^{13}$CH$_2$ | $^{13}$CD$_2$ | $^{13}$C |
| DiART$^9$-118 | CD$_2$H | CD$_2$H | N | $^{13}$C | $^{15}$N | $^{13}$CH$_2$ | $^{13}$CH$_2$ | $^{13}$C |
| DiART$^9$-119 | CD$_2$H | CD$_2$H | $^{15}$N | C | $^{15}$N | $^{13}$CH$_2$ | $^{13}$CH$_2$ | $^{13}$C |
| DiART$^9$-120 | CD$_3$ | CD$_3$ | N | $^{13}$C | N | $^{13}$CH$_2$ | $^{13}$CH$_2$ | C |
| DiART$^9$-121 | CD$_3$ | CD$_3$ | $^{15}$N | C | N | $^{13}$CH$_2$ | $^{13}$CH$_2$ | C |
| DiART$^9$-122 | $^{13}$CD$_3$ | $^{13}$CD$_3$ | N | $^{13}$C | N | CH$_2$ | CH$_2$ | C |
| DiART$^9$-123 | $^{13}$CD$_3$ | $^{13}$CD$_3$ | $^{15}$N | C | N | CH$_2$ | CH$_2$ | C |

Those positions containing heavy isotope atoms ($^{15}$N, $^{13}$C, $^2$H = D) in each reagent are shown in bold.

The reactive group of a DiART reagent is selected to react with a biomolecule of interest. In one embodiment the biomolecule is a protein or peptide. In another one embodiment the reactive group of a DiART reagent is a protein reactive group. In still another embodiment the reactive group is reactive with a functional group of a protein or peptide. In yet another embodiment the functional group is an amine.

In a specific embodiment, the invention relates to a DiART reagent comprising the general formula:

reporter group–balancer group–amine reactive group wherein the reporter group and the balancer group are linked by a an MS/MS scissionable bond and wherein the reactive group reacts with an amine.

In another embodiment the invention relates to a composition comprising one or more DiART reagents.

Another exemplary reagent of the invention is a DiART-like reagent comprising a thiol-reactive reactive group. Such reagents are termed DiART-t reagents. Examples of DiART-t reagents are provided by the following formulas:

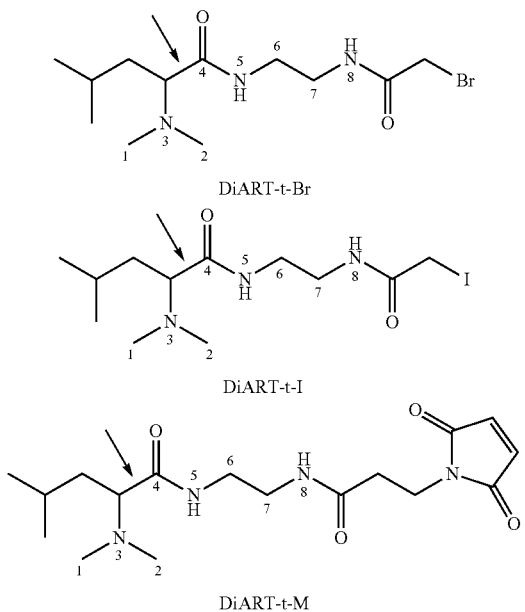

DiART-t-Br

DiART-t-I

DiART-t-M where any of positions 1-8 may be heavy isotope atoms and where the arrow indicates the fragmentation site between the reporter group and the balancer group (FIG. 1). The suffix —Br, —I or -M is indicative of the reactive group of various DiART-t reagents. DiART-t-Br comprises a bromoacetyl reactive group, DiART-t-I comprises an iodoacetyl reactive group, and DiART-t-M comprises a maleimide reactive group. These are exemplary DiART-t reagents and additional reactive groups are contemplated by the invention.

In the DiART-like reagents the reporter group is (CH$_3$)$_2$CH—CH$_2$—CH(N(CH$_3$)$_2$), the balancer group is CO—NH—CH$_2$—CH$_2$—NH, and the reactive group is Br—CH$_2$—CO (DiART-t-Br), I—CH$_2$—CO (DiART-t-I) or cyclo-N(CO—CH=CH—CO)—CH$_2$—CH$_2$—CO (DiART-t-M). The reporter group and the balancer group are linked by an MS/MS scissionable bond, the reporter group comprises 0 to 9 heavy isotope atoms selected from $^{15}$N and $^2$H, the balancer group comprises 0 to 9 heavy isotope atoms selected from $^{13}$C and $^2$H, and the reagent contains one or more $^2$H atoms. The CH$_3$ at position 1 has 0 to 4 heavy isotope atoms, selected from $^{13}$C and $^2$H; the CH$_3$ at position 2 has 0 to 4 heavy isotope atoms, selected from $^{13}$C and $^2$H; the N at position 3 is selected from $^{14}$N and $^{15}$N; the C at position 4 is selected from $^{12}$C and $^{13}$C; the N at position 5 is selected from $^{14}$N and $^{15}$N; the CH$_2$ at position 6 has 0 to 3 heavy isotope atoms, selected from $^{13}$C and $^2$H; the CH$_2$ at position 7 has 0 to 3 heavy isotope atoms, selected from $^{13}$C and $^2$H and the N at position 8 is selected from $^{14}$N and $^{15}$N. The mass of the reporter group is 114-123 Daltons, the mass of the balancer group is 86-95 Daltons, and the sum of the mass of the reporter group and the balancer group is 200-209 Daltons.

A DiART-like reagent of the invention with 1 heavy isotope has a reporter group with a mass of 114-115 Daltons and a balancer group with a mass of 86-87 Daltons, and the total mass of the reporter group and the balancer group is 201 Daltons. A DiART-like reagent of the invention with 2 heavy isotopes has a reporter group with a mass of 114-116 Daltons and a balancer group with a mass of 86-88 Daltons, and the total mass of the reporter group and the balancer group is 202 Daltons. A DiART-like reagent of the invention with 3 heavy isotopes has a reporter group with a mass of 114-117 Daltons and a balancer group with a mass of 86-89 Daltons, and the total mass of the reporter group and the balancer group is 203 Daltons. A DiART-like reagent of the invention with 4 heavy isotopes has a reporter group with a mass of 114-118 Daltons and a balancer group with a mass of 86-90 Daltons, and the total mass of the reporter group and the balancer group is 204 Daltons. A DiART-like reagent of the invention with 5 heavy isotopes has a reporter group with a mass of 114-119 Daltons and a balancer group with a mass of 86-91 Daltons, and the total mass of the reporter group and the balancer group is 205 Daltons. A DiART-like reagent of the invention with 6 heavy isotopes has a reporter group with a mass of 114-120 Daltons and a balancer group with a mass of 86-92 Daltons, and the total mass of the reporter group and the balancer group is 206 Daltons. A DiART-like reagent of the invention with 7 heavy isotopes has a reporter group with a mass of 114-121 Daltons and a balancer group with a mass of 86-93 Daltons, and the total mass of the reporter group and the balancer group is 207 Daltons. A DiART-like reagent of the invention with 8 heavy isotopes has a reporter group with a mass of 114-122 Daltons and a balancer group with a mass of 86-94 Daltons, and the total mass of the reporter group and the balancer group is 208 Daltons. A DiART-like reagent of the invention with 9 heavy isotopes has a reporter group with a mass of 114-123 Daltons and a balancer group with a mass of 86-95 Daltons, and the total mass of the reporter group and the balancer group is 209 Daltons.

In another embodiment the invention provides a group of DiART-like reagents, which are structurally identical and vary only by isotope composition. The selection of substituents in each of the reporter group and balancer group is made such that the change in mass attributable to the selection of substituents in the reporter group is offset by the change in mass attributable to the selection of substituents in the balancer group, and where the sum of the mass of the reporter group and the balancer group is equal in each of the isotopic variants.

In an exemplary embodiment, a DiART-like reagent has five heavy isotope atoms, four of which are $^2H$ atoms. Substituents in the reporter group of a DiART-like reagent are selected such that the mass of the reporter group is in the range of 114-119 Daltons, while the substituents of the balancer group of a DiART-like reagent are selected such that the mass of the balancer group is 86-91 Daltons and the sum of the mass of the reporter group and the balancer group is 205 Daltons.

In the exemplary embodiment, a group of six reagents can be prepared, where each of the DiART-like reagents is structurally identical, each containing a reporter, a balancer, and a reactive group, where the molecules vary only by isotopic composition. Each reagent contains five heavy isotope atoms. In DiART-t-114, the mass of the reporter group is 114 Daltons and the mass of the balancer group is 91 Daltons. In DiART-t-115, the mass of the reporter group is 115 Daltons and the mass of the balancer group is 90 Daltons. In DiART-t-116, the mass of the reporter group is 116 Daltons and the mass of the balancer group is 89 Daltons. In DiART-t-117, the mass of the reporter group is 117 Daltons and the mass of the balancer group is 88 Daltons. In DiART-t-118, the mass of the reporter group is 118 Daltons and the mass of the balancer group is 87 Daltons. In DiART-t-119, the mass of the reporter group is 119 Daltons and the mass of the balancer group is 86 Daltons. When the resulting reagents are fragmented in MS/MS, they generate strong reporter ions with MS peaks ranging from 114 to 119. Each of the reagents, termed $DiART^5$-t-114 to $DiART^5$-t-119, is set forth in Table 3 below:

TABLE 3

| Reagent | Position 1 | Position 2 | Position 3 | Position 4 | Position 6 | Position 7 |
|---|---|---|---|---|---|---|
| $DiART^5$-t-114 | $CH_3$ | $CH_3$ | $^{14}N$ | $^{13}C$ | $CD_2$ | $CD_2$ |
| $DiART^5$-t-115 | $CH_3$ | $CH_3$ | $^{15}N$ | $^{12}C$ | $CD_2$ | $CD_2$ |
| $DiART^5$-t-116 | $CH_2D$ | $CH_2D$ | $^{14}N$ | $^{13}C$ | $CD_2$ | $CH_2$ |
| $DiART^5$-t-117 | $CH_2D$ | $CH_2D$ | $^{15}N$ | $^{12}C$ | $CD_2$ | $CH_2$ |
| $DiART^5$-t-118 | $CHD_2$ | $CHD2$ | $^{14}N$ | $^{13}C$ | $CH_2$ | $CH_2$ |
| $DiART^5$-t-119 | $CHD_2$ | $CHD2$ | $^{15}N$ | $^{12}C$ | $CH_2$ | $CH_2$ |

Those positions containing heavy isotope atoms ($^{15}N$, $^{13}C$, $^2H$ = D) in each reagent are shown in bold.

The total mass of any of the DiART-t-Br reagents with five heavy isotope atoms, four of which are $^2H$ atoms is 326 Daltons (326.1337 Daltons when containing a $^{13}C$ or 326.1273 when containing a $^{15}N$). The total mass of any of the DiART-t-M reagents with five heavy isotope atoms, four of which are $^2H$ atoms is 357 Daltons (357.2395 Daltons when containing a $^{13}C$ or 357.2332 when containing a $^{15}N$). The total mass of any of the DiART-t-I reagents with five heavy isotope atoms, four of which are $^2H$ atoms is 374 Daltons (374.1198 Daltons when containing a $^{13}C$ or 374.1135 when containing a $^{15}N$).

While a group of six DiART-like reagents is provided as an exemplary embodiment herein, the invention also contemplates groups of additional numbers of DiART reagents that are isotopic variants of one another, where the sum of the mass of the reporter group and the balancer group is equal in each of the isotopic variants.

In another exemplary embodiment a group of ten reagents can be prepared, where each of the DiART-t reagents is structurally identical, each containing a reporter, a balancer, and a reactive group, where the molecules vary only by isotope composition. Each reagent contains five heavy isotope atoms. Exemplary reagents, termed $DiART^9$-t-114 to $DiART^9$-t-123, is set forth in Table 4 below:

TABLE 4

| Reagent | Position 1 | Position 2 | Position 3 | Position 4 | Position 5 | Position 6 | Position 7 | Position 8 |
|---|---|---|---|---|---|---|---|---|
| $DiART^9$-t-114 | $CH_3$ | $CH_3$ | N | $^{13}C$ | $^{15}N$ | $^{13}CD_2$ | $^{13}CD_2$ | $^{15}N$ |
| $DiART^9$-t-115 | $CH_3$ | $CH_3$ | $^{15}N$ | C | $^{15}N$ | $^{13}CD_2$ | $^{13}CD_2$ | $^{15}N$ |
| $DiART^9$-t-116 | $CDH_2$ | $CDH_2$ | N | $^{13}C$ | $^{15}N$ | $^{13}CH_2$ | $^{13}CD_2$ | $^{15}N$ |

TABLE 4-continued

| Reagent | Position 1 | Position 2 | Position 3 | Position 4 | Position 5 | Position 6 | Position 7 | Position 8 |
|---|---|---|---|---|---|---|---|---|
| DiART⁹-t-117 | CDH$_2$ | CDH$_2$ | $^{15}$N | C | $^{15}$N | $^{13}$CH$_2$ | $^{13}$CD$_2$ | $^{15}$N |
| DiART⁹-t-118 | CD$_2$H | CD$_2$H | N | $^{13}$C | $^{15}$N | $^{13}$CH$_2$ | $^{13}$CH$_2$ | $^{15}$N |
| DiART⁹-t-119 | CD$_2$H | CD$_2$H | $^{15}$N | C | $^{15}$N | $^{13}$CH$_2$ | $^{13}$CH$_2$ | $^{15}$N |
| DiART⁹-t-120 | CD$_3$ | CD$_3$ | N | $^{13}$C | N | $^{13}$CH$_2$ | $^{13}$CH$_2$ | N |
| DiART⁹-t-121 | CD$_3$ | CD$_3$ | $^{15}$N | C | N | $^{13}$CH$_2$ | $^{13}$CH$_2$ | N |
| DiART⁹-t-122 | $^{13}$CD$_3$ | $^{13}$CD$_3$ | N | $^{13}$C | N | CH$_2$ | CH$_2$ | N |
| DiART⁹-t-123 | $^{13}$CD$_3$ | $^{13}$CD$_3$ | $^{15}$N | C | N | CH$_2$ | CH$_2$ | N |

Those positions containing heavy isotope atoms ($^{15}$N, $^{13}$C, $^2$H = D) in each reagent are shown in bold.

The reactive group of a DiART-like reagent is selected to react with a biomolecule of interest. In one embodiment the reactive group of a DiART-like reagent is reactive with a functional group of the biomolecule. In another embodiment the functional group is a thiol.

In a specific embodiment, the invention relates to a DiART-t reagent comprising the general formula:

reporter group–balancer group–thiol reactive group wherein the reporter group and the balancer group are linked by an MS/MS scissionable bond and wherein the reactive group reacts with a thiol.

In another embodiment the invention relates to a composition comprising one or more DiART-like reagents.

In yet another embodiment the invention relates to a composition comprising one or more deuterium isobaric tag reagents. Such reagents include, but are not limited to DiART reagents and DiART-like reagents, such as DiART-t reagents. In one embodiment the composition comprises deuterium isobaric tag reagents that are isotopic variants of one another.

Figure 3:
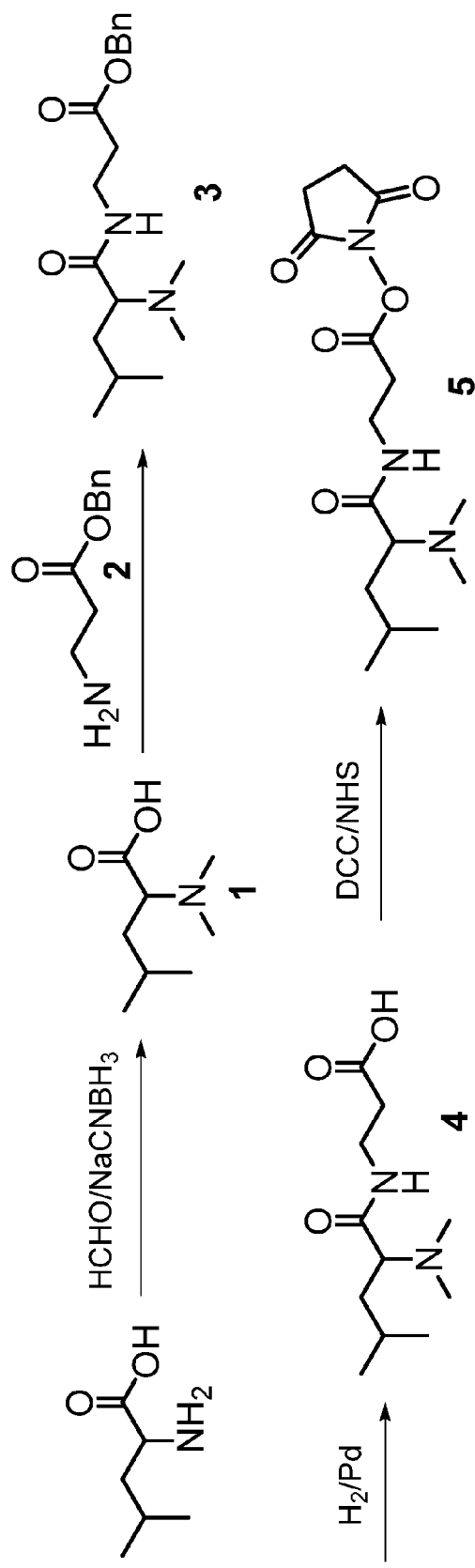
FIG. 3 is a schematic illustration of the general synthesis of DiART reagents.

In one embodiment the general synthesis of DiART reagents (FIG. 3) begins with the preparation of N,N'-dimethyl leucine 1 from leucine by standard reductive methylation conditions with formaldehyde and sodium cyanoborohydride. The N,N'-dimethyl leucine then reacts with β-alanine benzyl ester 2. The benzyl ester protecting group in Compound 3 is removed by hydrogenation and the newly exposed carboxylate group is activated by reacting with NHS and DCC to offer the final product, Compound 5. The detailed reaction conditions are provided in Example 1. FIG. 3 provides an illustration of a method used to specifically synthesize reagents 114-119.

The above process results in synthesis of DiART reagents with four steps and an overall yield of 30%~40%. Furthermore, all of the isotope labeled starting materials are quite inexpensive, making this synthetic route a very cost-effective approach to make DiART reagents.

By contrast, commercially available TMT reagents are prepared by a 14-step scheme and their overall yield is less than 1%, in addition to utilizing more expensive $^{13}$C— and $^{15}$N-labeled starting materials (PCT Publication No. WO2007/012849).

In another embodiment of the invention, in the initial synthesis step, leucine may be substituted by any other native amino acid without a functional group in its side chain. For example any of glycine, alanine, valine, and phenylalanine may be used alternatively to leucine.

Figure 4:
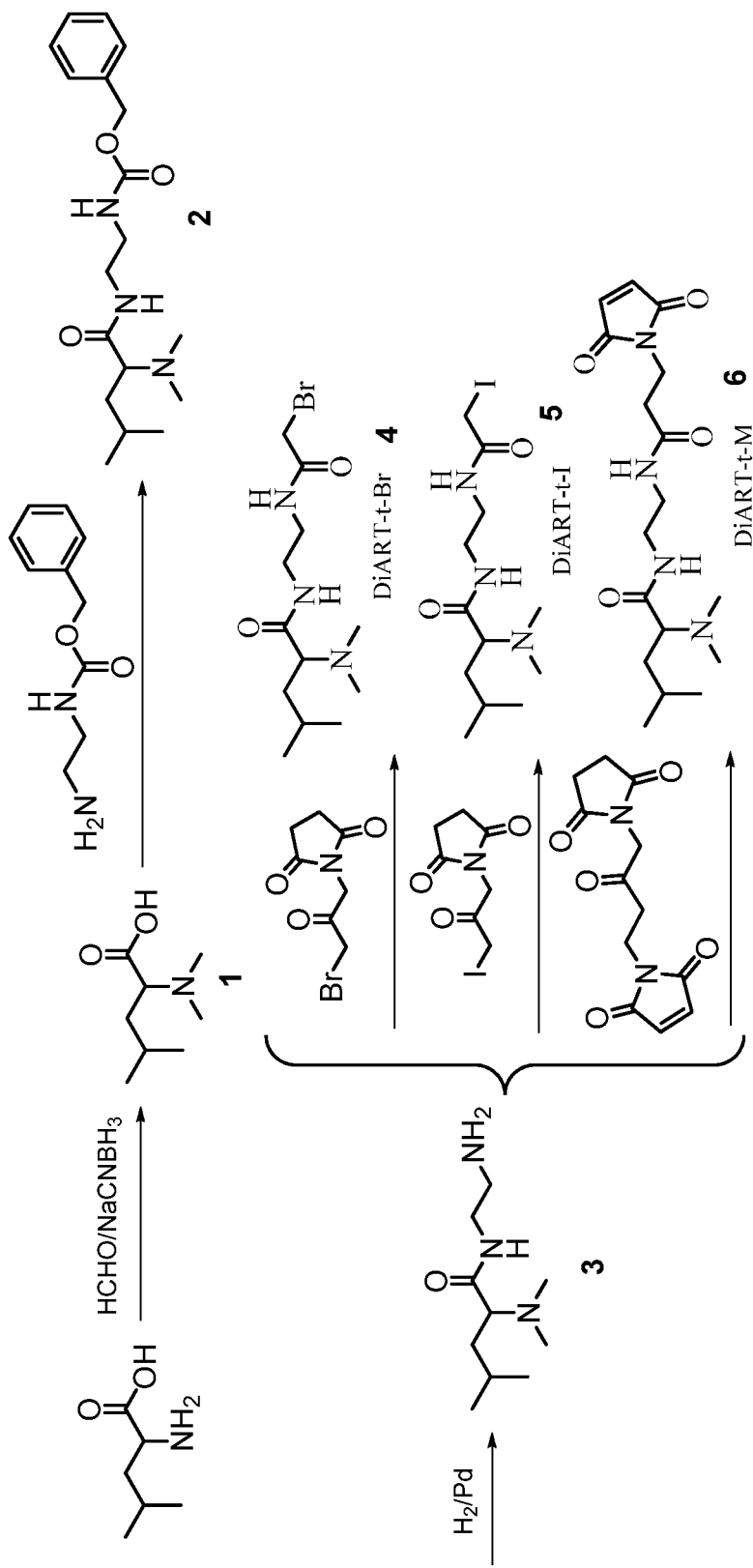
FIG. 4 is a schematic illustration of the general synthesis of DiART-t reagents.

In another embodiment FIG. 4 provides an illustration of a method used to specifically synthesize reagents DiART-t-Br. DiART-t-I and DiART-t-M. The detailed reaction conditions are provided in Example 2.

The reagents of the invention are useful for labeling or tagging of samples for biomolecular quantitation processes. As demonstrated herein, in an exemplary embodiment, where the reagents comprise five heavy isotopes, each of DiART and DiART-like reagents can exist in six structurally identical forms, which vary only by isotope composition. The reagents can be used to quantitate up to six biomolecular samples concurrently, using all of the six reagents.

The reagents of the invention can comprise 0 to 9 heavy isotope atoms, therefore reagents of the invention can be isotopic variants of other reagents of the invention. The invention further contemplates use of more than one reagent of the invention in parallel processes, where the one or more reagents may be used separately, in a group, or in a composition. In one embodiment the reagents present in a group or in a composition are isotopic variants of one another, such that when the reagents are fragmented in MS/MS, they generate strong reporter ions with MS peaks ranging from 114 to 123, depending on the number of heavy isotope atoms in the reporter group of the reagent.

The reagents can be added to the biomolecules to be quantitated by any known method. In one embodiment the biomolecules are proteins or peptides and the methods are proteomic methods.

Mass spectrometry (MS) is an exemplary quantitation process used for analysis of the composition of a sample or molecule. Reagents are used in the MS process to treat the sample or molecule for analysis. This application provides deuterium isobaric tag reagents that react with a sample via the reactive group and are subsequently fragmented between the reported group and the balancer group, to provide charged fragments that can be detected by MS.

In one embodiment the reagents are used in quantitative MS analysis. The reagents may be added to the biomolecular sample at the time of MS analysis or prior to analysis.

In another embodiment the reagents are useful in facilitation of processes and treatment of a biomolecular sample. In a particular embodiment the facilitation or treatment is carried out prior to MS analysis.

Analysis of a biomolecular sample that contains peptides, proteins or other biomolecules may be improved by filtration, separation or other pre-analytical process prior to the analysis. Such pre-analytical processes may include, but are not limited to, liquid chromatography (LC) and gel filtration (e.g. 2D gel electrophoresis) of the sample. In one embodiment of the invention the reagents are used to label the biomolecule prior to the pre-analytical process. In a particular embodiment, the biomolecule comprises a functional group that improves the pre-analytical processes.

Where deuterium isobaric tag reagents of the invention are used to label the biomolecule prior to the pre-analytical process, one or more samples can be combined or pooled with other labeled samples and can be subjected to the pre-analytical processes and the MS analysis simultaneously with additional samples. The ability to label samples with the deuterium isobaric tag reagents at the similar or an earlier step in the analytical process provides as good or better performance compared to existing stable isotope labeling methods, such as iTRAQ and TMT. Combination or pooling of multiple samples labeled with deuterium isobaric tag reagents of the invention provides results that can minimize, negate or even eliminate system errors that are seen with parallel analysis.

In one embodiment the invention provides a composition containing one or more deuterium isobaric tag reagents useful in biomolecular quantitation. In one embodiment the invention provides a composition of one or more DiART reagents. In another embodiment the invention provides a composition of one or more DiART-like reagents. In a further embodiment the invention relates to a method comprising use of one or more DiART reagents. In a still further embodiment the invention relates to a method comprising use of one or more DiART-t reagents.

Figure 5:
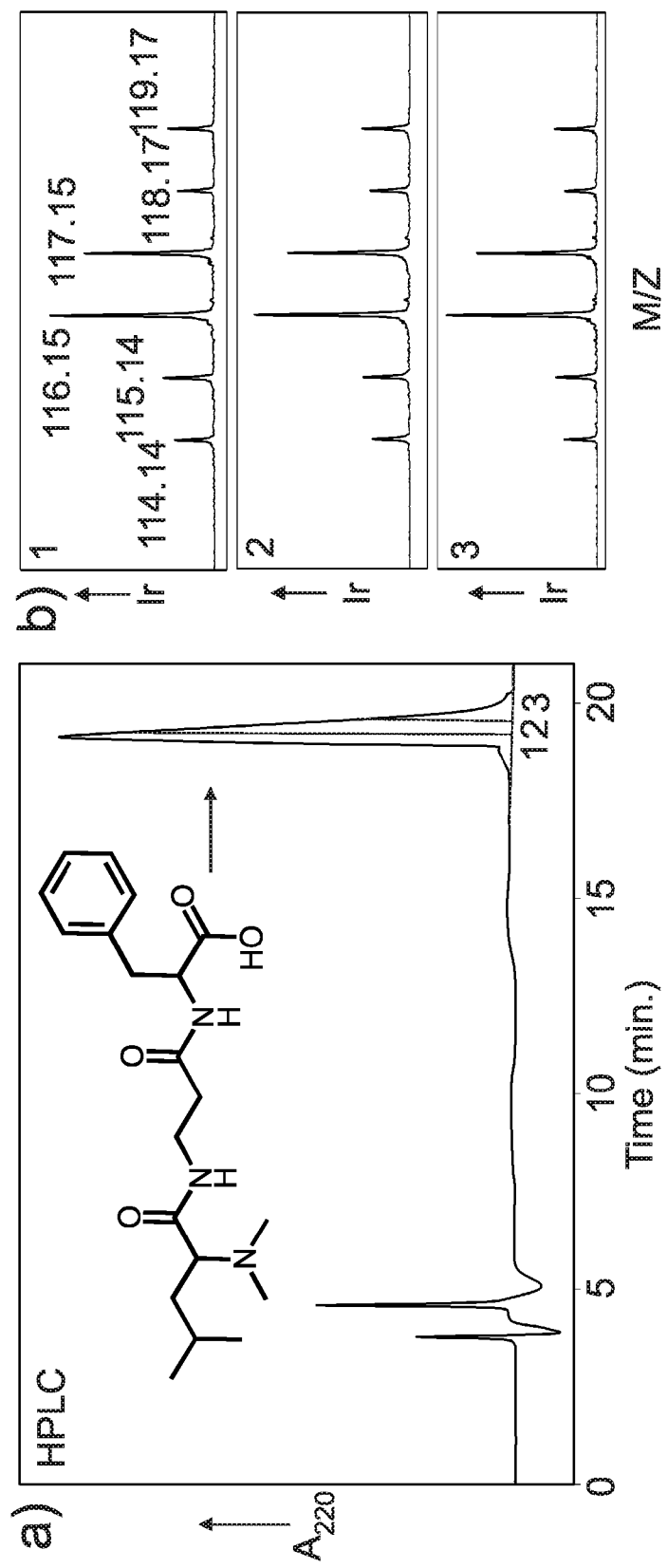
FIG. 5A is an HPLC chromatogram of a mixture of phenylalanines that are differentially labeled with six DiART tags and FIG. 5B are MS/MS spectra of three time fractions of the peak of FIG. 5A, as described in Example 4 below.

In an exemplary embodiment of DiART reagents, each of the DiART reagents can covalently attach to the free amine group of tryptic peptides and label them for MS/MS analysis. In the first MS analysis, identical peptides differentially labeled with DiART reagents are indistinguishable from each other, thereby exhibiting a single peak (see, for example, FIG. 5). However, once these precursor ions are fragmented in MS/MS, the fragmentation site in the tags is easily broken apart to produce a series of strong reporter ions ranging from 114 to 119, allowing biomolecular quantitation by comparing the intensities of the six reporter ions in the MS/MS spectra. Each DiART reagent also contains the same number of $^2$H atoms (four per molecule) that are placed next to hydrophilic groups, in order to eliminate $^2$H-related chromatographic isotope effects. By using $^2$H as a coding isotope, the synthesis of DiART is greatly simplified compared to that of iTRAQ and TMT tags.

A composition comprising six DiART-like reagents with five heavy isotope atoms and four $^2$H would be expected to produce similar results.

In one embodiment, deuterium isobaric tag reagents of the invention may be used in protein quantitation using the same principles as are utilized with iTRAQ and TMT (as each of those processes also provides a set of reagents).

Commercially available iTRAQ (Bantscheff, M. et al. Nat Biotechnol 2007, 25, 1035-44.) and TMT (tandem mass tag) (Dayon, L.; Hainard, A.; Licker, V.; Turck, N.; Kuhn, K.; Hochstrasser, D. F.; Burkhard, P. R.; Sanchez, J. C. Anal Chem 2008, 80, 2921-31.) isobaric tags also provide groupings of structurally identical molecules. iTRAQ are eight amine specific isobaric reagents that label the primary amines of peptides from up to eight different or replicate biological samples. The iTRAQ labeled peptides from each sample are mixed. Then the pooled samples are typically separated using two-dimensional liquid chromatography (LC) and analyzed using MS and tandem mass spectrometry (MS/MS). Because of the isobaric nature of these reagents, the peptides having the same sequence and mass from each sample appears as a single peak in the MS spectrum. Upon collision induced dissociation, the iTRAQ-tagged peptides fragment to release reporter ions (at 113.1, 114.1, 115.1, 116.1, 117.1, 118.1, 119.1, and 121.1 m/z) and b- and y-ion series among other fragments. The peak area of the reporter ions are used to assess relative abundance of peptides and consequently the proteins from which they are derived (Kunal Aggarwal et al., *Shotgun Proteomics Using the iTRAQ Isobaric Tags*, Briefings in Functional Genomics and Proteomics, 2006, 5, 122-120). The structure of the isobaric tag iTRAQ includes a reporter group that can contain 4-8 differentially tagged sites, allowing for mass differences of 1-8 Da. To maintain the total mass of the reporter plus balance components of the tag constant, differential isotopic labeling with $^{13}$C, $^{15}$N, and $^{16}$O atoms is used.

Although deuterium isobaric tag reagents of the invention are $^2$H labeled, peptide samples labeled with different deuterium isobaric tag reagents of the invention exhibit absolutely no chromatographic isotope shift (Example 4), demonstrating a performance as efficient as either of iTRAQ or TMT. More importantly, deuterium isobaric tag reagents of the invention can be synthesized easily from inexpensive starting materials, providing a much more cost-effective reagent than either of iTRAQ or TMT.

The deuterium isobaric tag reagents provided herein therefore make it feasible to perform MS-based tests on a vast number of clinical samples at a reasonable cost for the discovery of disease specific biomarkers and early diagnosis. This technology will not only outperform existing stable isotope labeling methods, iTRAQ and TMT, but also allow further expansion for the development of other novel reagents useful in quantitative proteomics.

The development of the deuterium isobaric tag reagents provided herein confirm that $^2$H-associated chromatographic isotope effects can be eliminated if $^2$H-containing molecules are properly designed. The protocol for protein identification and quantitation based on these reagents can be easily incorporated into Mascot, the most widely used software package for MS/MS data analysis. The deuterium isobaric tag reagents of the invention may also be useful in other types of mass spectrometers, such as ESI-based LTQ-Orbitrap. Therefore, deuterium isobaric tag reagents offer a cost-effective replacement for iTRAQ and TMT tags.

The advantages and features of the invention are further illustrated with reference to the following examples, which are not to be construed as in any way limiting the scope of the invention but rather as illustrative of one embodiment of the invention in a specific application thereof.

EXAMPLE 1

Synthesis of Non-Isotope Labeled DiART Reagents

DiART reagents were synthesized by following the scheme illustrated in FIG. 3.

Compound 1:

Formaldehyde (HCHO/DCDO, 16 mmol) was added into a suspension of leucine (2 mmol) in methanol (8 mL) and acetic acid (400 μL) at 0° C., followed by reductive reagent (sodium cyanoborohydride/deuteride, 5 mmol). The mixture was stirred at ambient temperature for 12 hours. It turned to clear solution after several hours. The methanol and excessive formaldehyde were removed in vacuo. The residue was taken up in methanol (20 mL) and dried with anhydrous $Na_2SO_4$. The concentrated syrup was used in the next step directly without further purification.

Compound 2:

A 250 mL Round-bottomed flask equipped with a reflux condenser was loaded with β-alanine (4.5 g, 50 mmol), benzyl alcohol (15 mL) and toluene (30 mL) at room temperature. p-Toluenesulfonic acid monohydrate (9.6 g, 50 mmol) was added under stiffing. The resulting solution was stirred under reflux for more than 10 hours and then cooled to ambient temperature overnight. Diethyl ether (100 mL) was added slowly and the mixture was cooled to 0° C. in refrigerator overnight, which resulted in precipitation of the product. The product was isolated by filtration, washed with ether (3×20 mL) and dried under reduced pressure, to give the desired compound (~16.8 g) in the form of a white crystalline product.

Compound 3:

N,N'-dicyclohexylcarbodiimide (DCC) was added into a solution of Compound 1 (2 mmol) and N-methylmorpholine (660 µL, 6 mmol) in dichloromethane (DCM) (30 mL) at 0° C. The resulting mixture was stirred at 0° C. for 2 min, and Compound 2 (660 mg, 2 mmol) was then added. The resulting white slurry was vigorously stirred at room temperature for 24 hours. After white precipitate was removed by filtration, the organic layer was washed with saturated aqueous $NaHCO_3$ solution and brine, dried over $Na_2SO_4$, filtered, concentrated under vacuum and run flash chromatograph purification to yield the desired compound as a colorless to yellowish oil (350 mg-550 mg, yield 75%-86%).

Compound 4:

Compound 3 was added into a solution of anhydrous methanol (20 mL) containing 5% Pd—C (150 mg). The resulting mixture was stirred under hydrogen gas balloon for 5 hours. The catalyst was filtered through a celite pad, washed with 2×10 mL methanol. The combined filtrate and washing solution were evaporated under reduced pressure to give Compound 4 (150 mg-200 mg, yield 60%). The white solid was washed with diethyl ether (20 mL) to remove low boiling point impurity.

Compound 5:

Compound 4 (130 mg, 0.57 mmol) and N-hydroxysuccinimide (65 mg, 0.65 mmol) were suspended in DCM (10 mL). Then, DCC was added at 0° C. and the reaction was stirred under $N_2$ for at least 15 hours. After white precipitate was filtered out, the reaction mixture was then washed with saturated $NaHCO_3$ (2×20 mL) and brine (20 mL). The organic layer was dried with anhydrous $Na_2SO_4$ and the solvent was removed in vacuo, to get the product as off-white to yellowish solid.

To synthesize DiART reagents with distinct reporter mass, different isotope-labeled starting materials were used. Table 5 provides details regarding the isotope-labeled starting materials for DiART reagents, as described above.

EXAMPLE 2

Synthesis of Non-Isotope Labeled DiART-T Reagents

DiART-t reagents were synthesized by following the scheme illustrated in FIG. 4.

Compound 1:

Formaldehyde (HCHO/DCDO, 16 mmol) was added into a suspension of leucine (2 mmol) in methanol (8 mL) and acetic acid (400 µL) at 0° C., followed by reductive reagent (sodium cyanoborohydride/deuteride, 5 mmol). The mixture was stirred at ambient temperature for 12 hours. It turned to clear solution after several hours. The methanol and excessive formaldehyde were removed in vacuo. The residue was taken up in methanol (20 mL) and dried with anhydrous $Na_2SO_4$. The concentrated syrup was used in the next step directly without further purification.

Compound 2:

N,N'-dicyclohexylcarbodiimide (DCC) was added into a solution of Compound 1 (2 mmol) and N-methylmorpholine (660 µL, 6 mmol) in dichloromethane (DCM) (30 mL) at 0° C. The resulting mixture was stirred at 0° C. for 2 min, and mono N-Benzyloxycarbonyloxy-ethylenediamine (388 mg, 2 mmol) was then added. The resulting white slurry was vigorously stirred at room temperature for 24 hours. After white precipitate was removed by filtration, the organic layer was washed with saturated aqueous $NaHCO_3$ solution and brine, dried over $Na_2SO_4$, filtered, concentrated under vacuum and run flash chromatograph purification to yield the desired compound as a colorless or yellowish oil.

Compound 3:

Compound 2 was added into a solution of anhydrous methanol (20 mL) containing 5% Pd—C (150 mg). The resulting mixture was stirred under hydrogen gas balloon for 5 hours. The catalyst was filtered through a celite pad, washed with 2×10 mL methanol. The combined filtrate and washing solution were evaporated under reduced pressure to give Compound 4 (100 mg-150 mg, yield 80%). The white solid was washed with diethyl ether (20 mL) to remove low boiling point impurity.

TABLE 5

| | DiART-114 | DiART-115 | DiART-116 | DiART-117 | DiART-118 | DiART-119 |
|---|---|---|---|---|---|---|
| Leu-OH | $1\text{-}^{13}C$ | $^{15}N$ | $1\text{-}^{13}C$ | $^{15}N$ | $1\text{-}^{13}C$ | $^{15}N$ |
| HCHO | unlabeled | unlabeled | unlabeled | unlabeled | DCDO | DCDO |
| $NaCNBH_3$ | unlabeled | unlabeled | $NaCNBD_3$ | $NaCNBD_3$ | unlabeled | unlabeled |
| β-Ala-OH | (D,D,D,D structure) | (D,D,D,D structure) | (D,D structure) | (D,D structure) | unlabeled | unlabeled | where $D = {}^2H$.
$1\text{-}^{13}C$ and $^{15}N$ labeled leucine were purchased from Cambridge Isotope Laboratory, Inc.
DCDO and $NaCNBD_3$ were purchased from Sigma.
$D_4$-β-alanine was purchased from C/D/N Isotopes Inc.
$D_2$-β-alanine was synthesized in house (Hanai, K.; Kuwae, A. *J. Labelled Comp. Rad.*, 1988, 25, 217-224.).

Compound 4:

Compound 4 (101 mg, 0.5 mmol) and N-succinimidyl bromoacetate (117 mg, 0.5 mmol) were dissolved in acetonitrile (10 mL). Then, triethylamine (1 mmol) was added at 0° C. and the reaction was stirred under $N_2$ for at least 15 hours. The reaction mixture was then washed with saturated $NaHCO_3$ (2×20 mL) and brine (20 mL). The organic layer was dried with anhydrous $Na_2SO_4$ and the solvent was removed in vacuo, to get the product as off-white to yellowish solid. Compound 5 and compound 6 will be synthesized similarly by reacting Compound 4 with N-succinimidyl iodoacetate and N-(β-Maleimidopropyloxy) succinimide ester, respectively.

To synthesize DiART reagents with distinct reporter mass, different isotope-labeled starting materials will be used. Table 6 provides details regarding the isotope-labeled starting materials for DiART reagents, as described above.

TABLE 6

|  | DiART-t-114 | DiART-t-115 | DiART-t-116 | DiART-t-117 | DiART-t-118 | DiART-t-119 |
|---|---|---|---|---|---|---|
| Leu-OH | 1-$^{13}$C | $^{15}$N | 1-$^{13}$C | $^{15}$N | 1-$^{13}$C | $^{15}$N |
| HCHO | unlabeled | unlabeled | unlabeled | unlabeled | DCDO | DCDO |
| NaCNBH$_3$ | unlabeled | unlabeled | NaCNBD$_3$ | NaCNBD$_3$ | unlabeled | unlabeled |
| Ethylenediamine | NH$_2$CD$_2$CD$_2$NH$_2$ | NH$_2$CD$_2$CD$_2$NH$_2$ | NH$_2$CD$_2$CH$_2$NH$_2$ | NH$_2$CD$_2$CH$_2$NH$_2$ | NH$_2$CH$_2$CH$_2$NH$_2$ | NH$_2$CH$_2$CH$_2$NH$_2$ | where D = $^2$H.

EXAMPLE 3

Isotope Purity of DiART Reagents

The isotope purity of each DiART reagent synthesized as above was determined by fragmenting the reagent in a LTQ-Orbitrap MS/MS spectrometer and measuring intensity of all peaks between 114 and 121. Table 7 provides the results of isotope purity from one batch of DiART reagents. These values are included in a configuration file on a Mascot server to correct quantitation error caused by isotope impurities.

TABLE 7

| Δ(M/Z) | −2 | −1 | 0 | +1 | +2 |
|---|---|---|---|---|---|
| DiART-114 | 0.000 | 0.000 | 0.985 | 0.015 | 0.000 |
| DiART-115 | 0.000 | 0.008 | 0.987 | 0.005 | 0.000 |
| DiART-116 | 0.000 | 0.010 | 0.982 | 0.008 | 0.000 |
| DiART-117 | 0.000 | 0.009 | 0.979 | 0.012 | 0.000 |
| DiART-118 | 0.000 | 0.005 | 0.980 | 0.015 | 0.000 |
| DiART-119 | 0.000 | 0.006 | 0.985 | 0.009 | 0.000 |

EXAMPLE 4

Elimination of $^2$H Isotope Effects Using DiART Reagents

To demonstrate the DiART reagents can eliminate $^2$H isotope effects in reverse phase HPLC, six different amount of phenylalanine were reacted with each excess DiART reagent in a mixture (NaHCO$_3$, 50 mM, and 1,4-dioxane, 50%), respectively, mixed, and then purified with $C_{18}$-HPLC (Buffer A: water, 0.1% TFA; Buffer B: acetonitrile, 0.1% TFA; gradient: 0-6 mins 10% B, 6-8 mins 10% to 20% B, 8-48 mins 20% B to 60% B; flow rate; 1 mL/min). A single broad peak of the product was observed ($A_{220}$=absorbance at 220 nm) (FIG. 5A). Three time fractions (1-3) of this peak were collected and analyzed with MALDI-MS/MS, which generated the reporter ions with identical relative intensities. MS/MS spectra of three fractions are provided in FIG. 5B. Each spectrum has six reporter ion peaks (114.14, 115.14, 116.15, 117.15, 118.17, 119.17). Ir=relative intensity. M/Z=mass-to-charge ratio. These spectra imply that DiART labeled phenylalanine residues co-eluted and were irresolvable by HPLC. Because phenylalanine can be considered as a single-residue peptide, these results confirmed that DiART labeled tryptic peptides would not display any chromatographic shift.

EXAMPLE 5

Protein Quantitation With DiART Reagents and Mascot Software

To make DiART reagents useful for proteomics applications, they must be compatible with standard MS/MS data analysis programs used for protein identification, such as Mascot (Perkins, D. N.; Pappin, D. J.; Creasy, D. M.; Cottrell, J. S. Electrophoresis 1999, 20, 3551-67) and SEQUEST. (Eng, J. K.; McCormack, A. L.; Yates, J. R. J. Am. Soc. Mass Spectrom. 1994, 5, 976-989). DiART reagents were tested with Mascot because this database search engine is widely used in proteomics community and its latest release (version 2.2) includes new features for protein quantitation that can be easily modified to fit different needs. To demonstrate protein quantitation with DiART reagents and Mascot software, bovine serum albumin (20 μg), bovine catalase (20 μg), and chicken ovalbumin (10 μg) were dissolved in 100 μL denaturing/reducing solution (8 M urea, 50 mM Sodium borate buffer, pH=8.3, 5 mM TCEP) and incubated at 37° C. for 30 mins. Then, 20 mM 2-bromoacetamide was added to alkylate free cysteine residues. The proteins were precipitated with acetone, dissolved again in 100 μL buffer (200 mM Sodium borate buffer, pH=8.3, 0.8 M urea), and then digested with trypsin (10 μg) at 37° C. overnight. Six 10-μL fractions of samples were mixed with 20 μL DiART reagents (2 mg/mL in acetonitrile), respectively and the reaction was incubated at room temperature for 4 hours. All of six samples were then mixed together, dried in a SpeedVac, then dissolved again in a SCX (strong ion exchange) loading buffer (10 mM KH$_2$PO$_4$, pH=3.0, 25% acetonitrile). This sample was loaded onto a SCX column, washed, and eluted with 500 μL elution buffer (10 mM KH$_2$PO$_4$, pH=3.0, 400 mM KCl, 25% acetonitrile). The elution was dried in SpeedVac and dissolved in 100 μL 5% acetonitrile. 4 μL of labeled peptide sample was injected into a capillary reverse phase HPLC (gradient, 5% acetonitrile, 0.1% TFA to 50% acetonitrile, 0.1% TFA in 60 mins; column, Agilent Zorbax $C_{18}$, 5 µm, 150×0.5 mm; flow rate, 15 µL/min) (FIG. 6A; $A_{220}$=absorbance at 220 nm) and each fraction was analyzed with ABI-4700 MALDI-MS/MS. The peak lists containing their m/z values and intensities extracted from MS data were sent to a Mascot server to obtain both the identity and the quantity of peptides simultaneously.

Figure 6:
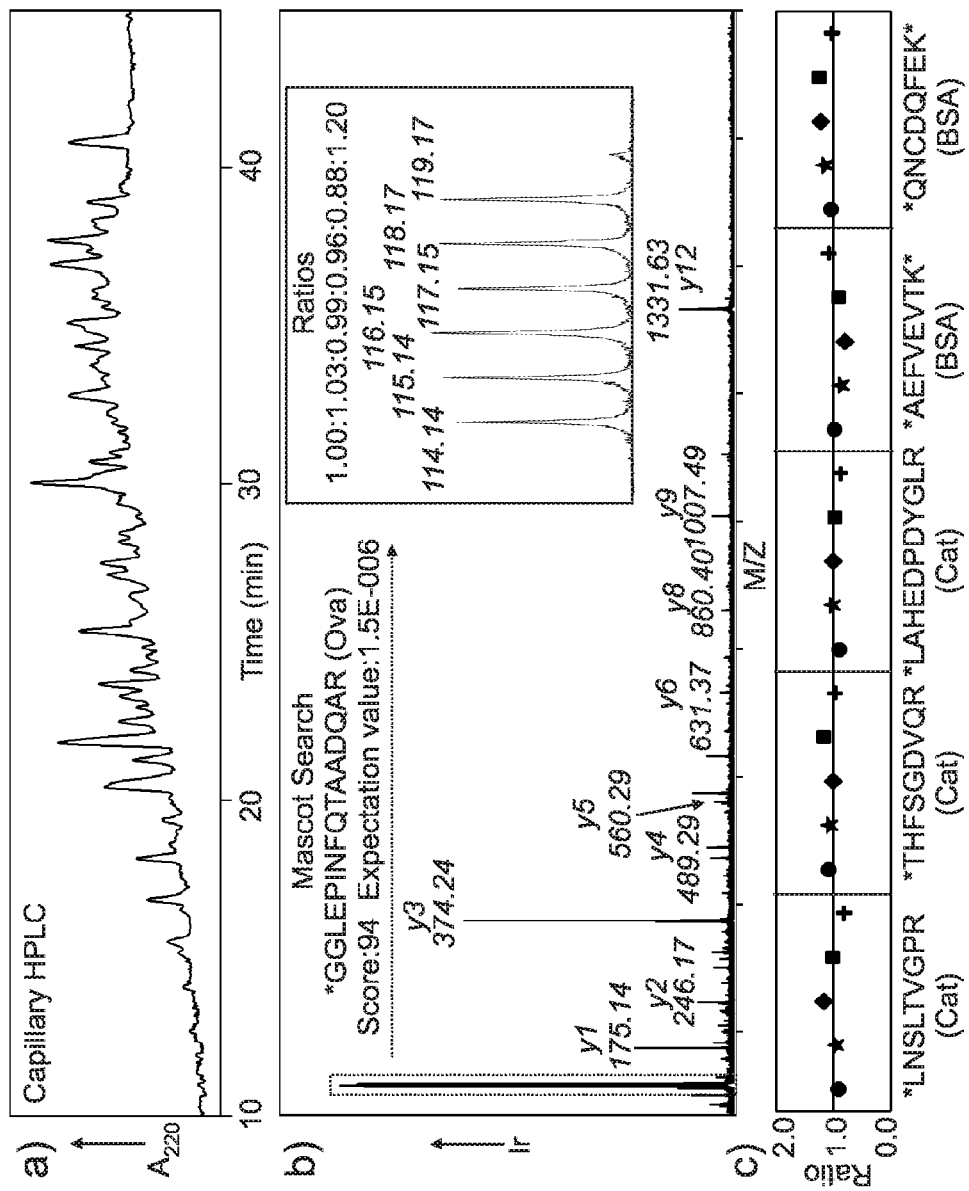
FIG. 6A is a capillary HPLC chromatogram of the tryptic peptide mixture of Example 5 after DiART labeling.
FIG. 6B is a MS/MS spectrum of one peptide chosen from chicken ovalbumin (Ova)
FIG. 6C shows the relative ratios of reporter ions from several other peptides, as described in Example 5.
Figure 7:
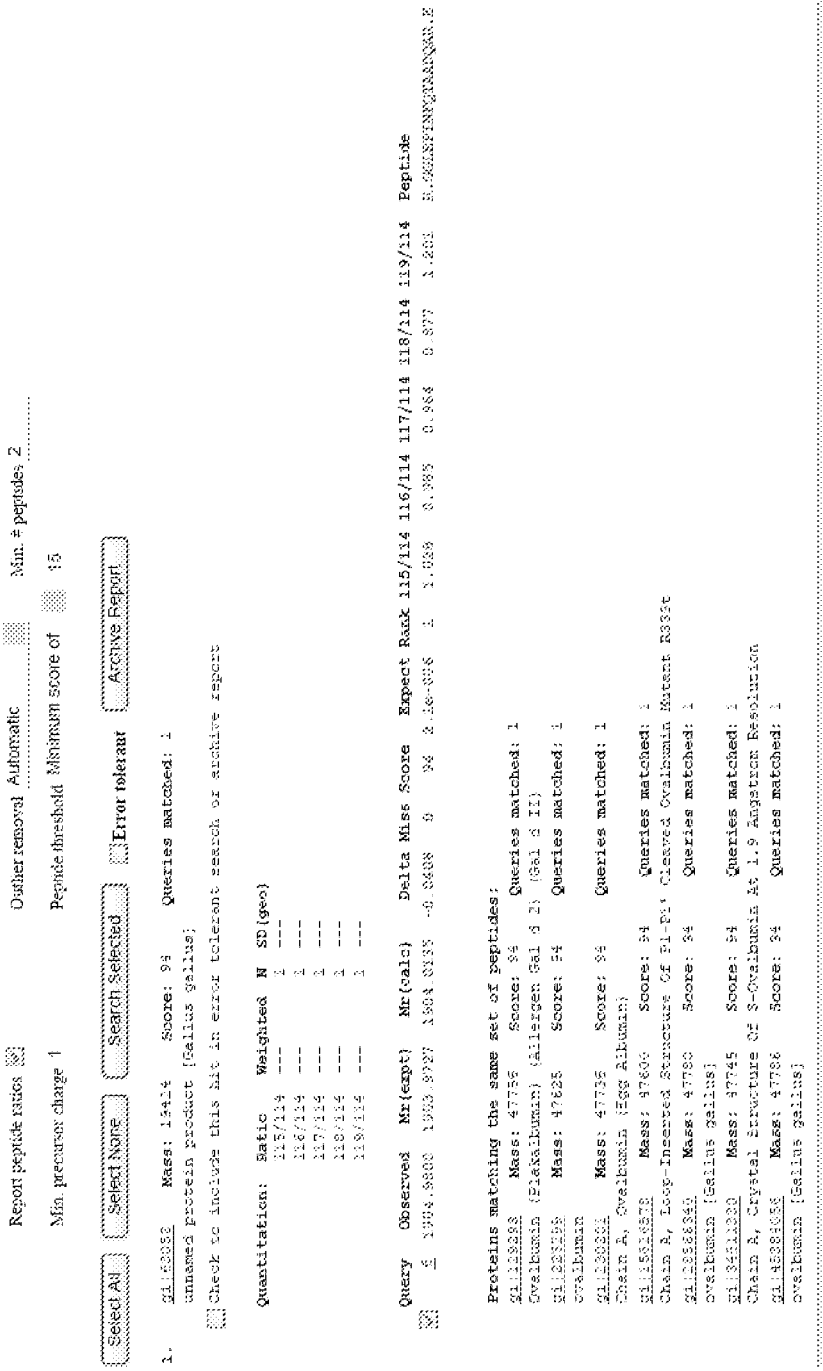
FIG. 7 provides exemplary Mascot search results.

For example, a peptide (Ova) from chicken ovalbumin (GGLEPINFQTAADQAR) was recognized with a score of 88 and an expectation value of $7\times10^{-7}$, indicating this is a high-confidence assignment. Meanwhile, the relative abundance of this peptide labeled with different DiART reagents was obtained at a 0.94:0.98:1.17:1.00:0.97:1.21 ratio after the isotope impurity of DiART reagents was calibrated (FIG. 6B), representing only a small deviation from the predefined 1:1:1:1:1:1 ratio (Shadforth, I. P.; Dunkley, T. P.; Lilley, K. S.; Bessant, C. BMC Genomics 2005, 6, 145.). In FIG. 6B, the asterisk on the N-terminus of the peptide sequence indicates it is labeled with DiART tags. This peptide was identified by Mascot with high confidence score. Those b and y fragments are indicated. The inlet is the expanded spectrum in the range of 113-121. The relative ratios of six reporter ions were also obtained from Mascot. (Ir=relative intensity. M/Z=mass-to-charge ratio.)

After many other peptides were quantified similarly to obtain enough data that are statistically meaningful, the average coefficients of variation of DiART labeling were calculated as about 0.15 (FIG. 6C). FIG. 6C shows the relative ratios (from left to right in each: 115/114, 116/114, 117/114, 118/114, and 119/114) of reporter ions from the several other peptides whose sequences and origins are shown. (BSA=bovine serum albumin. Cas=bovine β-casein. Cat=bovine catalase). The calculated coefficient of 0.15 is comparable to commercially available, more expensive TMT and iTRAQ tags (Chong, P. K.; Gan, C. S.; Pham, T. K.; Wright, P. C. J Proteome Res 2006, 5, 1232-40). In addition, it was observed that the fragmentation site in the DiART reagents was exceptionally easy to fragment and the reporter ions were usually predominating peaks in most MS/MS spectra, greatly contributing to the accuracy of quantitation because these signature peaks have high signal-to-noise ratios.

While the invention has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A deuterium isobaric tag reagent (DiART) reagent comprising the formula:

reporter group–balancer group–reactive group wherein the reporter group comprises $(CH_3)_2$—CH—$CH_2$—CH—$(N(CH_3)_2)$, the balancer group comprises CO—(NH)—$CH_2$—$CH_2$—CO, the reactive group comprises cyclo-N(CO—$CH_2$—$CH_2$—CO)—O, and the reagent has the structure:

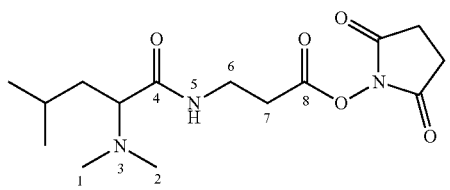 [SMILES: CC(C)CC(C(=O)NCCC(=O)ON1C(=O)CCC1=O)N(C)C]

wherein the reporter group and the balancer group are linked by a MS/MS scissionable bond, the reporter group comprises 0 to 9 heavy isotope atoms selected from $^{13}C$, $^{15}N$ and $^{2}H$, the balancer group comprises 0 to 9 heavy isotope atoms selected from $^{13}C$, $^{15}N$ and $^{2}H$, the reagent contains 1 to 6 $^{2}H$ atoms, and wherein the $CH_3$ at position 1 comprises 0 to 3 $^{2}H$ atoms and the C is selected from $^{12}C$ and $^{13}C$, the $CH_3$ at position 2 comprises 0 to 3 $^{2}H$ atoms and the C is selected from $^{12}C$ and $^{13}C$, the N at position 3 is selected from $^{14}N$ and $^{15}N$, the C at position 4 is selected from $^{12}C$ and $^{13}C$, the N at position 5 is selected from $^{14}N$ and $^{15}N$, the $CH_2$ at position 6 comprises 0 to 2 $^{2}H$ atoms and the C is selected from $^{12}C$ and $^{13}C$, the $CH_2$ at position 7 comprises 0 to 2 $^{2}H$ atoms and the C is selected from $^{12}C$ and $^{13}C$, the C at position 8 is selected from $^{12}C$ and $^{13}C$;

and wherein the mass of the reporter group is 114-123 Daltons, the mass of the balancer group is 99-108 Daltons, and the sum of the mass of the reporter group and the balancer group is 214-222 Daltons.

2. A composition comprising two or more DiART reagents of claim 1, wherein each of the two or more DiART reagents are isotopic variants of one another and the sum of the mass of the reporter group plus the balancer group is the same in each isotopic variant.

3. The composition of claim 2, comprising six DiART reagents, each comprising five heavy isotope atoms.

4. The composition of claim 3, comprising $DiART^5$-114, $DiART^5$-115, $DiART^5$-116, $DiART^5$-117, $DiART^5$-118, and $DiART^5$-119.

5. A method of biomolecular quantitation, the method comprising the steps of:
a) adding a composition of claim 2 to a sample containing a biomolecule of interest, wherein the reactive group of the reagents reacts with the biomolecule of interest;
b) fragmenting the reagents; and
c) quantitating the biomolecule of interest.

6. A method of biomolecular quantitation, the method comprising the steps of:
a) adding a DiART reagent of claim 1 to a sample containing a biomolecule of interest, wherein the reactive group of the reagent reacts with the biomolecule of interest;
b) fragmenting the reagent; and
c) quantitating the biomolecule of interest.

7. A method of biomolecular quantitation, the method comprising the steps of:
a) adding two or more DiART reagents of claim 1 to a sample containing a biomolecule of interest, wherein each of the two or more DiART reagents are isotopic variants of one another and the sum of the mass of the reporter group plus the balancer group is the same in each isotopic variant and wherein the reactive group of the reagents reacts with the biomolecule of interest;
b) fragmenting the reagents; and
c) quantitating the biomolecule of interest.

8. The method of claim 7, wherein fragmenting the reagents comprises MS/MS.

9. A DiART-like reagent comprising the formula:

reporter group–balancer group–reactive group wherein the reporter group comprises $(CH_3)_2CH-CH_2-CH(N(CH_3)_2)$, the balancer group comprises $CO-NH-CH_2-CH_2-NH$, the reactive group comprises $Br-CH_2-CO$ (DiART-t-Br), $I-CH_2-CO$ (DiART-t-I) or cyclo-$N(CO-CH=CH-CO)-CH_2-CH_2-CO$ (DiART-t-M), and the reagent is selected from structures a), b) and c):

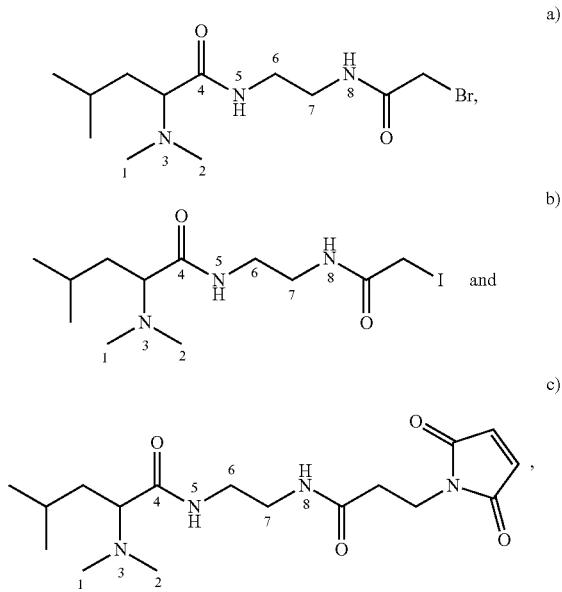

wherein the reporter group and the balancer group are linked by a MS/MS scissionable bond, the reporter group comprises 0 to 9 heavy isotope atoms selected from $^{13}C$, $^{15}N$ and $^2H$, the balancer group comprises 0 to 9 heavy isotope atoms selected from $^{13}C$, $^{15}N$ and $^2H$, the reagent contains 1 to 6 $^2H$ atoms, and
wherein the $CH_3$ at position 1 comprises 0 to 3 $^2H$ atoms and the C is selected from $^{12}C$ and $^{13}C$, the $CH_3$ at position 2 comprises 0 to 3 $^2H$ atoms and the C is selected from $^{12}C$ and $^{13}C$, the N at position 3 is selected from $^{14}N$ and $^{15}N$, the C at position 4 is selected from $^{12}C$ and $^{13}C$, the N at position 5 is selected from $^{14}N$ and $^{15}N$, the $CH_2$ at position 6 comprises 0 to 2 $^2H$ atoms and the C is selected from $^{12}C$ and $^{13}C$, the $CH_2$ at position 7 comprises 0 to 2 $^2H$ atoms and the C is selected from $^{12}C$ and $^{13}C$, the N at position 8 is selected from $^{14}N$ and $^{15}N$; and
wherein the mass of the reporter group is 114-123 Daltons, the mass of the balancer group is 86-95, and the sum of the mass of the reporter group and the balancer group is 200-209 Daltons.

10. A composition comprising two or more DiART-like reagents of claim 9, wherein each of the two or more DiART-like reagents are isotopic variants of one another and the sum of the mass of the reporter group plus the balancer group is the same in each isotopic variant.

11. The composition of claim 10, comprising six DiART-like reagents, each comprising five heavy isotope atoms.

12. The composition of claim 11, comprising DiART$^5$-t-114, DiART$^5$-t-115, DiART$^5$-t-116, DiART$^5$-t-117, DiART$^5$-t-118, and DiART$^5$-t-119.

13. A method of biomolecular quantitation, the method comprising the steps of:
a) adding a composition of claim 10 to a sample containing a biomolecule of interest, wherein the reactive group of the reagents reacts with the biomolecule of interest;
b) fragmenting the reagents; and
c) quantitating the biomolecule of interest.

14. A method of biomolecular quantitation, the method comprising the steps of:
a) adding a DiART-like reagent of claim 9 to a sample containing a biomolecule of interest, wherein the reactive group of the reagents reacts with the biomolecule of interest;
b) fragmenting the reagents; and
c) quantitating the biomolecule of interest.

15. A method of biomolecular quantitation, the method comprising the steps of:
a) adding of two or more DiART-like reagents of claim 9 to a sample containing a biomolecule of interest, wherein each of the two or more DiART-like reagents are isotopic variants of one another and the sum of the mass of the reporter group plus the balancer group is the same in each isotopic variant and wherein the reactive group of the reagents reacts with the biomolecule of interest;
b) fragmenting the reagents; and
c) quantitating the biomolecule of interest.

16. The method of claim 15, wherein the fragmenting the reagents comprises MS/MS.

17. A method of making a DiART reagent comprising the formula:

reporter group–balancer group–reactive group wherein the reporter group comprises $(CH_3)_2-CH-CH_2-CH-(N(CH_3)_2)$, the balancer group comprises $CO-(NH)-CH_2-CH_2-CO$, the reactive group comprises cyclo-$N(CO-CH_2-CH_2-CO)-O$, and the reagent has the structure:

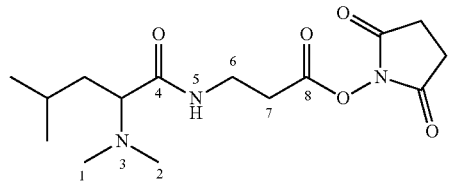

wherein the reporter group and the balancer group are linked by a MS/MS scissionable bond, the method comprising the steps of:
a) preparing N,N'-dimethyl-leucine by reacting leucine with formaldehyde and sodium cyanoborohydride;
b) reacting β-alanine benzyl ester with N,N'-dimethyl-leucine;
c) removing the benzyl ester protecting group from the compound resulting from step b) by hydrogenation; and
d) preparing activated carboxylate group of the compound resulting from step c) by reacting with N-hydroxysuccinimide (NHS) and N,N'-dicyclohexylcarbodiimide (DCC).

18. A method of making a DiART-t reagent comprising the formula:

reporter group–balancer group–reactive group wherein the reporter group comprises $(CH_3)_2CH-CH_2-CH(N(CH_3)_2)$, the balancer group comprises CO—NH—CH$_2$—CH$_2$—NH, the reactive group comprises Br—CH$_2$—CO (DiART-t-Br), I—CH$_2$—CO (DiART-t-I) or cyclo-N(CO—CH=CH—CO)—CH$_2$—CH$_2$—CO (DiART-t-M), and the reagent is selected from structures a), b) and c):

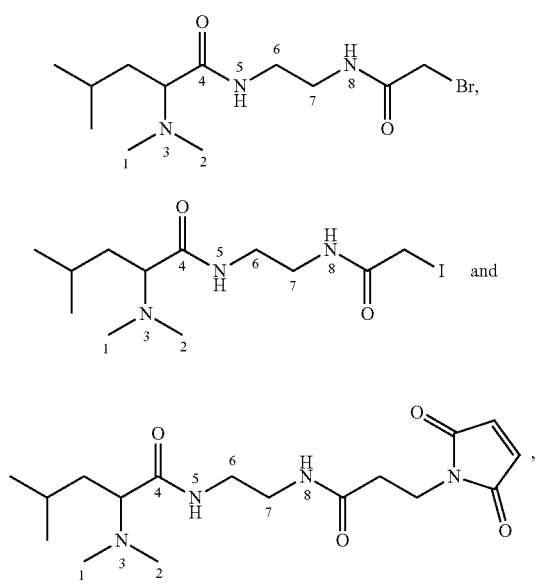

wherein the reporter group and the balancer group are linked by a MS/MS scissionable bond, the method comprising the steps of:
 a) preparing N,N'-dimethyl-leucine by reacting leucine with formaldehyde and sodium cyanoborohydride;
 b) reacting mono N-Benzyloxycarbonyloxy-ethylenediamine with N,N'-dimethyl-leucine;
 c) removing the N-Benzyloxycarbonyloxy protecting group from the compound resulting from step b) by hydrogenation; and
 d) preparing DiART-t reagents from the compound resulting from step c) by reacting with N-succinimidyl bromoacetate, or N-succinimidyl iodoacetate, or N-(β-Maleimidopropyloxy) succinimide ester, respectively.

19. A deuterium isobaric tag reagent comprising the formula:

reporter group–balancer group–reactive group wherein the reporter group comprises (CH$_3$)$_2$—CH—CH$_2$—CH—(N(CH$_3$)$_2$), the balancer group comprises CO—(NH)—CH$_2$—CH$_2$—CO, and the reagent has the structure:

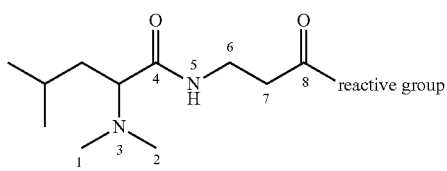

wherein the reporter group and the balancer group are linked by a MS/MS scissionable bond, the reporter group comprises 0 to 9 heavy isotope atoms selected from $^{13}$C, $^{15}$N and $^2$H, the balancer group comprises 0 to 9 heavy isotope atoms selected from $^{13}$C, $^{15}$N and $^2$H, the reagent contains 1 to 6 $^2$H atoms, the mass of the reporter group is from 114-123 Daltons, and the reactive group is reactive with a biomolecule, and wherein the reactive group is selected from the group consisting of:

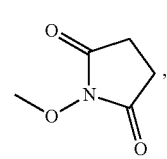

wherein the mass of the reporter group is 114-123 Daltons, the mass of the balancer group is 99-108 Daltons, and the sum of the mass of the reporter group and the balancer group is 214-222 Daltons,

wherein the mass of the reporter group is 114-123 Daltons, the mass of the balancer group is 86-95, and the sum of the mass of the reporter group and the balancer group is 200-209 Daltons

wherein the mass of the reporter group is 114-123 Daltons, the mass of the balancer group is 86-95, and the sum of the mass of the reporter group and the balancer group is 200-209 Daltons; and

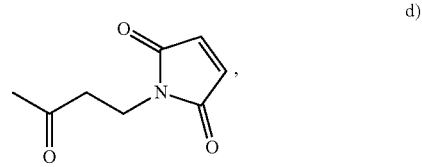

wherein the mass of the reporter group is 114-123 Daltons, the mass of the balancer group is 86-95, and the sum of the mass of the reporter group and the balancer group is 200-209 Daltons.

* * * * *

UNITED STATES PATENT AND TRADEMARK OFFICE
CERTIFICATE OF CORRECTION

PATENT NO. : 8,486,712 B2
APPLICATION NO. : 13/255849
DATED : July 16, 2013
INVENTOR(S) : Shuwei Li et al.

It is certified that error appears in the above-identified patent and that said Letters Patent is hereby corrected as shown below:

In the Specification

In column 12, Table 3, in the second to last row of the column titled "Position 2":
   "CHD2"
should be
   --$CHD_2$--

In column 12, Table 3, in the last row of the column titled "Position 2":
   "CHD2"
should be
   --$CHD_2$--

In the Claims

In column 24, lines 35-36,
   "...the reactive group comprises cyclo-N(CO-$CH_2$-CH,-CO)-O..."
should be
   --...the reactive group comprises *cyclo*-N(CO-$CH_2$-$CH_2$-CO)-O... --

Signed and Sealed this
Twenty-fourth Day of September, 2013

Teresa Stanek Rea
*Deputy Director of the United States Patent and Trademark Office*